(12) United States Patent
Kuniholm et al.

(10) Patent No.: US 11,672,678 B2
(45) Date of Patent: Jun. 13, 2023

(54) VARIABLE COMPLIANCE PROSTHETIC SOCKET WITH BREATHABLE MATRIX

(71) Applicant: Stumpworx LLC, Portland, OR (US)

(72) Inventors: Jonathan Kuniholm, Portland, OR (US); Zachary Meyer, Portland, OR (US)

(73) Assignee: Stumpworx LLC, Portland, OR (US)

( * ) Notice: Subject to any disclaimer, the term of this patent is extended or adjusted under 35 U.S.C. 154(b) by 0 days.

(21) Appl. No.: 16/974,120

(22) Filed: Oct. 5, 2020

(65) Prior Publication Data

US 2021/0298928 A1    Sep. 30, 2021

Related U.S. Application Data

(60) Provisional application No. 62/911,232, filed on Oct. 5, 2019.

(51) Int. Cl.
*A61F 2/80* (2006.01)
*A61F 2/76* (2006.01)
*A61F 2/50* (2006.01)

(52) U.S. Cl.
CPC .......... *A61F 2/80* (2013.01); *A61F 2/76* (2013.01); *A61F 2002/503* (2013.01)

(58) Field of Classification Search
CPC .. A61F 2/76; A61F 2/7812; A61F 2/80; A61F 2002/5003; A61F 2002/5043; A61F 2002/5016

See application file for complete search history.

(56) References Cited

U.S. PATENT DOCUMENTS

| 8,323,353 B1 | 12/2012 | Alley et al. |
| 8,978,224 B2 | 3/2015 | Hurley et al. |

(Continued)

FOREIGN PATENT DOCUMENTS

| CA | 2304743 A1 | 11/2000 |
| CA | 2325607 A1 | 5/2002 |

(Continued)

OTHER PUBLICATIONS

Alley et al., "Prosthetic Sockets Stabilized by Alternating Areas of Tissue Compression and Release," 48 JRRD. 679-96 (2010).

(Continued)

*Primary Examiner* — Christie Bahena
(74) *Attorney, Agent, or Firm* — Kolitch Romano Dascenzo Gates LLC

(57) ABSTRACT

A socket for engaging a residual limb includes a plurality of hard counters, each configured to engage the residual limb at defined "go points". The go points can bear pressure without discomfort or impeding range of motion. The counters are further configured to avoid contact with identified "no go" points where excess tissue may inhibit motion or experience irritation upon movement and which include one or more contoured pads to more effectively engage the bony prominences of the limb without inhibiting motion. A chassis from which each of the counters may flexibly depend connects the residual limb mechanically to a limb extension. A lacing system alternately intersects the counters and terminates in a tensioning reel. Rotation of the tensioning reel in a first direction will draw the laces over each of the counters such that the tensioned laces will draw counters together to engage the residual limb.

21 Claims, 14 Drawing Sheets

(56) References Cited

U.S. PATENT DOCUMENTS

| | | | |
|---|---|---|---|
| 9,044,349 B2 | 6/2015 | Hurley et al. | |
| 9,549,828 B2 | 1/2017 | Hurley et al. | |
| D778,452 S | 2/2017 | Cespedes et al. | |
| 10,123,888 B2 | 11/2018 | Alley et al. | |
| 10,179,056 B2 | 1/2019 | Hurley et al. | |
| 10,278,837 B1 | 5/2019 | Martin | |
| 10,369,027 B2 | 8/2019 | Alley | |
| 10,543,112 B2 | 1/2020 | Bache et al. | |
| 2011/0071647 A1* | 3/2011 | Mahon | A61F 2/76 623/33 |
| 2011/0208321 A1* | 8/2011 | Doddroe | A61F 2/7812 623/36 |
| 2012/0101597 A1* | 4/2012 | Bache | A61F 2/78 623/33 |
| 2014/0121783 A1* | 5/2014 | Alley | A61F 2/80 623/33 |
| 2015/0073567 A1* | 3/2015 | Wilson | A61F 2/60 623/33 |
| 2015/0366678 A1* | 12/2015 | Edwards | A61F 2/585 623/57 |
| 2017/0128238 A1 | 5/2017 | Hurley et al. | |
| 2017/0151072 A1 | 6/2017 | Mahon et al. | |
| 2020/0163783 A1 | 5/2020 | Martin | |

FOREIGN PATENT DOCUMENTS

| | | | | |
|---|---|---|---|---|
| DE | 102018111442 A1 | * | 11/2019 | ........... A61F 2/5046 |
| ES | 2642964 T3 | | 11/2017 | |
| FR | 3029101 A1 | * | 6/2016 | ............. A61F 2/588 |
| WO | WO-2006138388 A2 | * | 12/2006 | ............... A61F 2/54 |
| WO | 2018144736 A1 | | 8/2018 | |

OTHER PUBLICATIONS

Mutnick, Ally, "McCormick Freshman Design Prosthetic Arms for Amputee Patients," The Daily Northwestern (Jan. 9, 2013), https://dailynorthwestern.com/2013/01/09/campus/mccormick-freshmen-design-prosthetic-arms-for-amputee-patients/.

Miguelez et al., "The Transradial Anatomically Contoured (TRAC) Interface: Design Principles and Methodology," 15 JPO. 148-57 (2003).

Paterno et al., "Sockets for Limb Prostheses: A Review of Existing Technologies and Open Challenges," 65 IEEE. 1996-2010 (Sep. 2018).

Sokolowski et al., "A Product Design Ap3304proach to Prosthetic Design: A Case Study," 3304 DMD Proc. (2019).

English language machine-translation of Spain Patent Application Publication No. ES2642964T3, published Nov. 20, 2017.

* cited by examiner

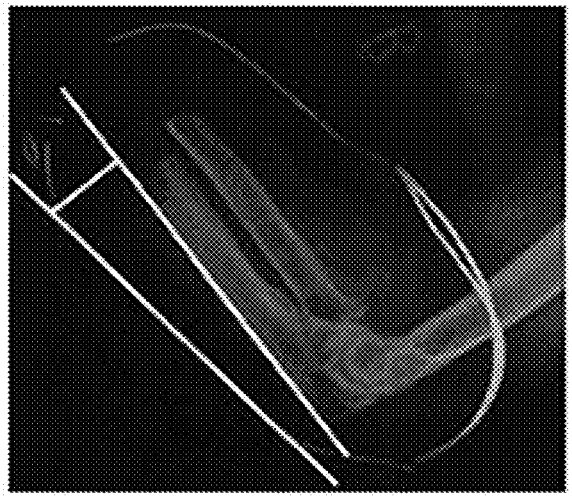
Fig. 2A    (Prior Art)
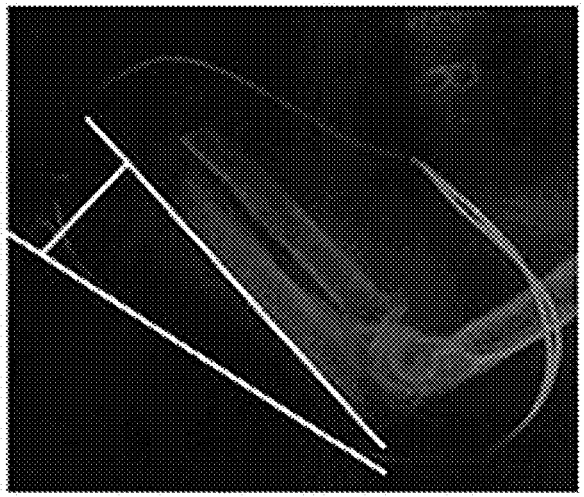
Fig. 2B    (Prior Art)
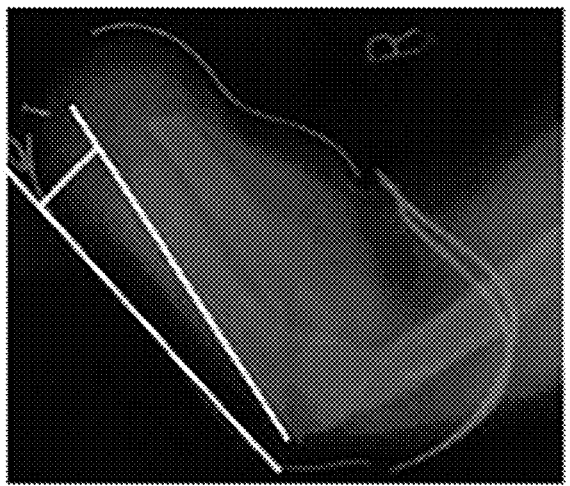
Fig. 3A    (Prior Art)
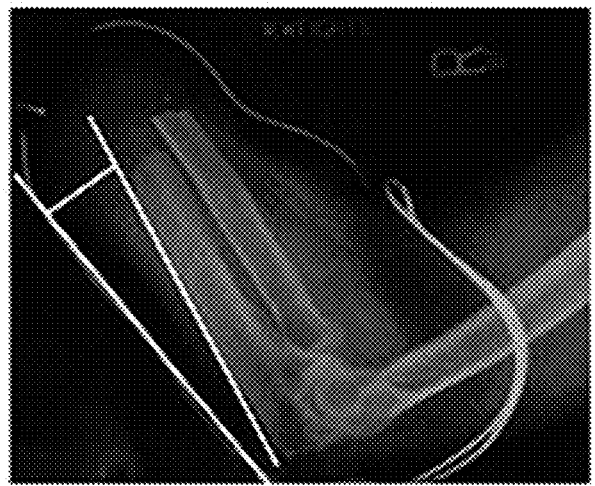
Fig. 3B    (Prior Art)

Lateral

Anterior

Medial

Posterior

Fig. 7A
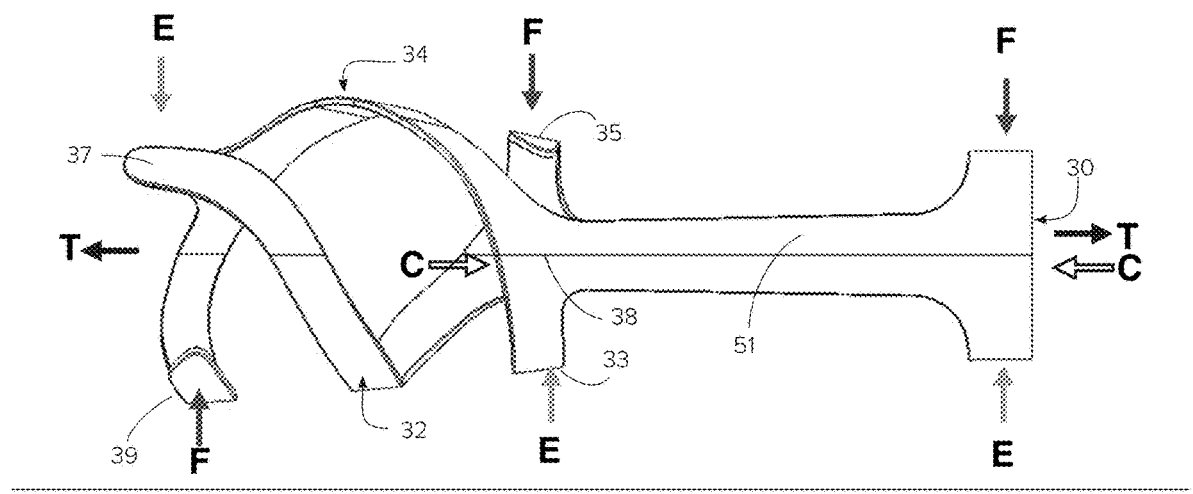
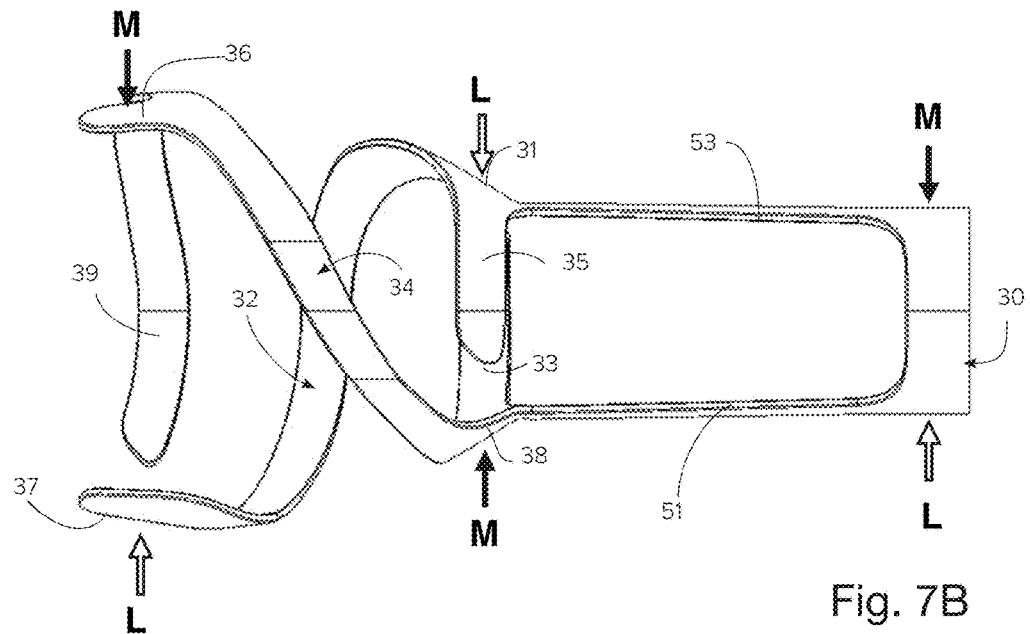
Fig. 7B

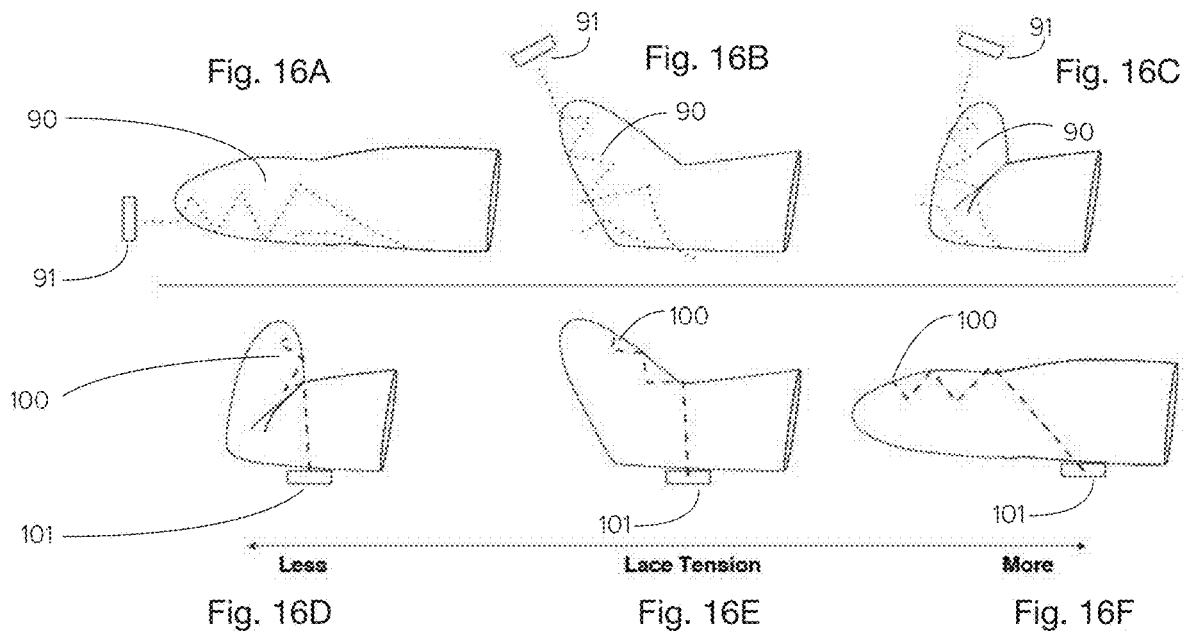
Fig. 16A Fig. 16B Fig. 16C
Fig. 16D Fig. 16E Fig. 16F
Less ← Lace Tension → More
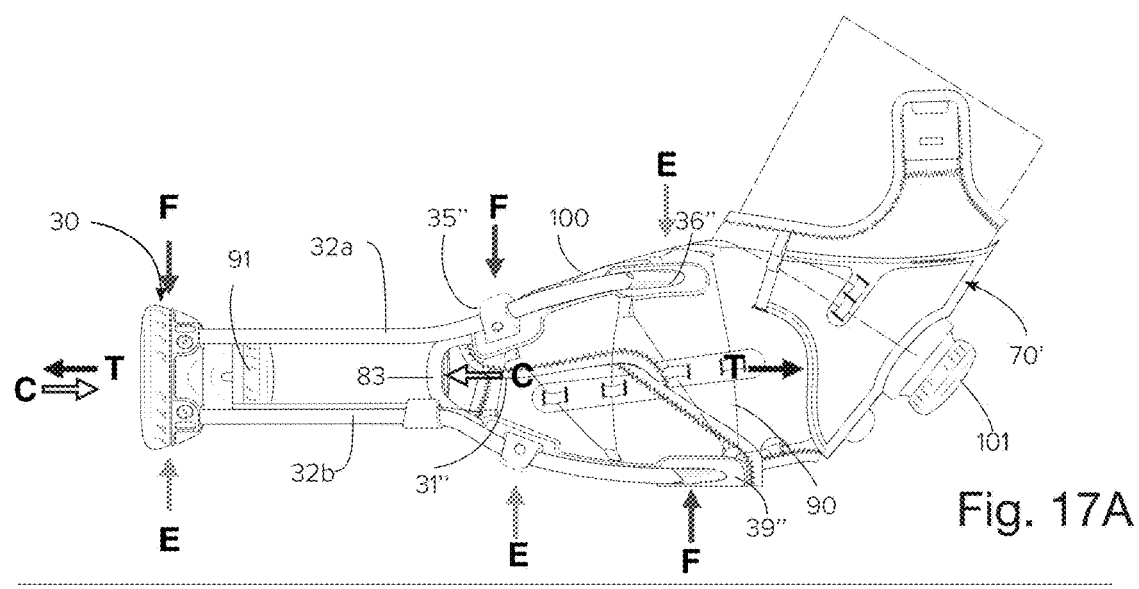
Fig. 17A
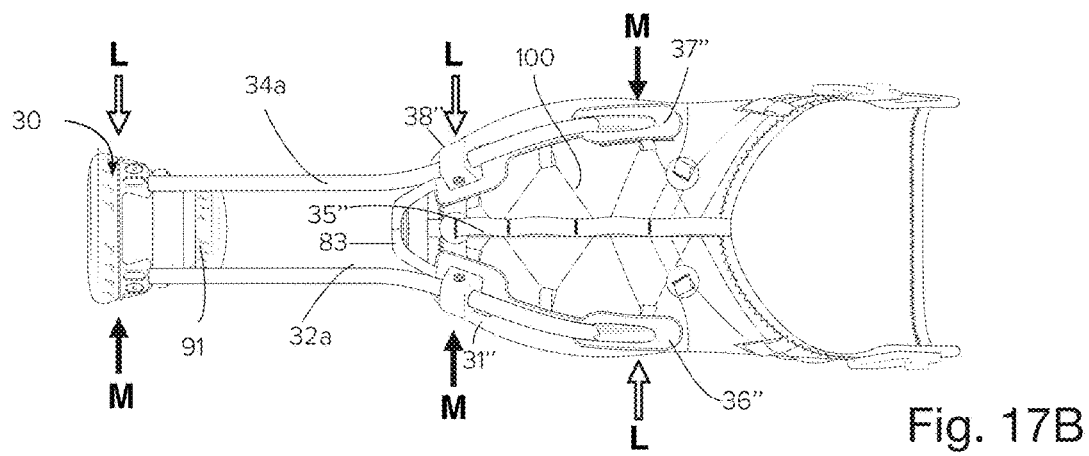
Fig. 17B

VARIABLE COMPLIANCE PROSTHETIC SOCKET WITH BREATHABLE MATRIX

REFERENCE TO RELATED APPLICATIONS

This application claims an invention which was disclosed in Provisional Application No. 62/911,232, filed on 5 Oct. 2019, entitled "Variable Compliance Joint-Transiting Soft Prosthetic Socket". The application claims the benefit under 35 U.S.C. § 119(e) of the United States provisional application and the aforementioned application is hereby incorporated herein by reference as if set out here in full.

FIELD OF THE INVENTION

The invention pertains to the field of limb prosthesis. More particularly, the invention pertains to structural configuration of such protheses.

BACKGROUND OF THE INVENTION

Among the general population, nearly half of all arm amputees either rejects or has never worn a prosthetic arm. Dissatisfaction stems from discomfort resulting from limb contact with the prosthetic suspension or interface (i.e., the point of attachment to the body). Such complaints represent the most frequent reasons for which users reject prostheses. The next most frequent complaint relates to a lack of function when employed once attached to the limb. While leg amputees are more likely to accept prostheses, they have similar complaints about conventional prostheses.

Suspension security (i.e. how well the limb is attached to the body and how accurately motion is transmitted and weight borne), and the amputee's comfort in use significantly affect the magnitude of weight the amputee will tolerate. Security and comfort present practical limits to amputees' acceptance of new technology. Both socket comfort and suspension security are adversely affected by poor heat and moisture management. These factors as well as harness discomfort represent significant specific complaints related to the comfort of wearing an upper limb prosthesis (Biddiss and Chau, J Rehabil Res Dev 2007). These same factors often cause suspension failure.

While the instant application is not limited to unpowered arms (more correctly referred to as "body-powered" as the amputee will assert movement by flexure of selected muscles), the presentation herein will remove any complexity necessary to facilitate powered prosthesis. The same configuration as disclosed herein will relate to both, as well as to legs. Such an exemplary body-powered embodiment is appropriate as such is the most commonly used type of upper limb harness. There exists a significant shortcoming in the prior art in that comfort of the harness is the most frequently cited objection (Biddiss and Chau, J Rehabil Res Dev 2007). In such a prosthesis, a harness provides both the control functionality and the superior tensile load-bearing capability of a body-powered arm prosthesis. Reasons for an amputee rejecting a harness include imparting of excess axillary pressure and a resulting neuropathy, as well as bulkiness, appearance over clothing, comfort of wearing the prosthesis under such clothing, a recurrent odor generated from repeated wearing (even despite cleaning), and difficulties in cleaning.

Given the very high rejection rate among arm amputees, clinicians have cobbled together numerous configurations to improve upon the existing convention. Among these configurations include self-suspending transradial sockets. Common to the existing convention is the need for a harness to enhance suspension as no socket entirely distal to the elbow joint can provide fully secure suspension. Self-suspending sockets, therefore, must rely for support on anatomy proximal to the elbow. Compromises as to either comfort or suspension security have been employed to replace the suspension provided by a harness by bridging the elbow with either a hard socket or a suction sleeve and pin lock. The downsides of such compromises are a resulting restriction on mobility and as well as poor moisture management. Such hard sockets are so close fitting that the limb cannot be pushed into the socket, and must be donned using a "donning sock," which is essentially a fabric shoehorn that pulls the limb tissue into the socket, exiting through a hole in the end.

At the center of the design problem is the goal of securing, in nonlimiting example, the arm against forces resulting from the amputee's use thereof. Extended arm or tensile loads in these compromise designs load the strap encircling the epicondyles of the humerus, move until the strap is pressed hard against the epicondyles, and can generally slip off the single angle at which it is possible to fit the elbow into the socket. Transverse loads, either by force directed by the arm against an object or from a load supported by the terminal device or prosthesis, exert force on the prosthetic socket and ultimately the residual limb inside the socket. In use, each rigid part of any prosthetic socket will move until stopped by one or multiple contacts between the residual limb and the inside of the socket, and then until the bone has displaced any intervening soft tissue. As illustrated in the prior art portrayed in FIGS. 2A, 2B, 3A, and 3B, a transverse load supported by the elbow in flexion results in a distal medial load, along with a more proximal dorsal load. In the case of a supporting a static load, reaction forces on the limb and socket form "force couples" that apply pressure at pairs of points on the residual limb. A native arm, in contrast, maintains a direct, intimate and lossless connection through the bone to the more distal part of the limb that grasps the load (a force and a moment at each point in the bone one might chose to examine).

Of the conventional self-suspending arm designs, the one allowing the greatest range of motion as found in published quantitative results relative to known prior art is the Transradial Anatomically Contoured (TRAC) socket (FIGS. 3A and 3B), the design of which was published by the team at Advanced Arm Dynamics (Miguelez, Lake et al. 2003). Despite its improvement over others, the TRAC socket still offers only 68 percent of anatomical range of motion. Other conventional designs include the Muenster socket (FIGS. 2A and 2B), the Northwestern socket, and various of the sockets by Randy Alley including the compression/release stabilized (CRS) socket, the anatomically contoured and controlled interface (ACCI), and the "Hi Fidelity Interface" (Alley, Williams III et al. 2011). Alley's designs are highly windowed variations of the same concepts, with the addition of significant tissue displacement to better register the long bones, but are still monolithic and limit range of motion. There are no quantitative published results on Alley's designs.

The existing prior art fails to adequately present a socket sufficient to resist skewing movement of the socket relative to the limb while at the same time allowing sufficient movement of the most distal joint. Conventional sockets transfer forces from the limb to the terminal device as directly as possible, with movement of the limb in the socket and of the bone displacing soft tissue translated into undesired movement of the limb relative to the terminal device.

In the case of self-suspending sockets, where a moving joint is crossed, such movement is the only way that motion of the joint can occur at all. These two objectives are in direct opposition to each other, and guarantee failure and compromise to some degree in each when using this approach.

Conventional sockets currently either created by prosthetists as custom design or the "off the shelf" configurable designs are little more than monolithic sockets with material cut away in varying degrees. These cuts are primarily longitudinal and are often cut in the form of "windows" in the socket, e.g. at the elbow. In the most extreme examples, most of the socket is removed, and small areas of the original footprint of a monolithic socket remain, as in Jay Martin's published patent application (US20180153716A1). Even in these designs, all the different versions of monolithic sockets are the product of removal of material in varying degrees.

Current conventional research and development efforts in prosthetic arm design are focused mainly on powered robotic movement and the various control improvements. Yet, the most functional prostheses most amputees use are body-powered devices. But each design approach still must address the interface between the socket and the residual limb with drawbacks in comfort and efficiency of movement solved in various ways by design of sockets and harnesses. While body-powered arm harnesses were discussed most frequently in the context of transradial arms as the instant invention, harnesses can exist at every other level of amputation, including legs, and are absolutely necessary at some. Indeed, the most common criticisms of even the most advanced prosthetic limbs of any type tend to surround the suspension of the devices rather than the devices themselves. Thus, there exists in the art a need for a change in socket design and construction that more effectively addresses inefficiencies of conventional prosthetic sockets, as well curing the significant defects in comfort that prevent amputees' from accepting and using prosthesis in daily life.

SUMMARY OF THE INVENTION

Embodiments of the instant invention improve prosthetic suspension over conventional hard socket and rubber liner systems. Relative to the instant invention, conventional prosthetic devices offer low or no-load bearing capacity, suffer from significantly reduced range of motion, poor heat and moisture management, pressure, and poor volume compensation, any of which might cause friction and tissue breakdown on the residual limb. Embodiments of the instant invention provide a more intimate engagement with limb tissue without impeding its comfort or efficiency in load bearing and range of motion.

Embodiments of the instant invention are configured to provide a secure, efficient and comfortable attachment of a rigid terminal device or foot to the body, preserving a range of motion. It is created by inserting the residual limb into a system consisting of multiple rigid counters, a variable compliance matrix of layers with different mechanical properties, and a lacing system to securely attach and adjust the system to the limb. These principles can be applied to a limb absence at any joint of the body, as well as embodiments with details that apply to specific instances of limb absence. Embodiments of the instant invention engage selected surfaces of the residual limb; the architecture of a socket the instant invention comprises exploits this selective engagement with points specific to the anatomy of the residual limb that are able to accept loading and pressure. These selected engagement points will be referred to in this instant application as "go" areas. Throughout this application, a second term will refer to those areas that cannot be impeded for reasons of freedom of movement or comfort; that second term is "no-go" areas. At each joint, the "go" areas roughly correspond to surfaces that are offset along the axis of rotation of the joint from the plane in which rotation occurs, though not exclusively. Likewise, "no-go" areas generally occur within or adjoining the plane of rotation in that such areas correspond to those surfaces of the limb of the joint at which skin and tissue must compress and expand during motion.

To exploit the "go" areas, the term "counter" will be used to describe semi-rigid batten-like structures that engage these "go" surfaces for optimal support and control while causing minimal interference. The socket comprises a plurality of these stiff members or counters, each of which connects a plurality of "go areas" without transiting or engaging "no-go" areas. The "go" areas may be better engaged by one or more pads with stiff contoured cores to better engage the boney prominences of the limb. Additional pads may cover other areas of the counters where they contact the limb. One or more lacing systems, parts of which may function as flexible hinges across joints, connect the counters and pads, combining and reinforcing their engaging effects, also without encroaching on no-go areas of the limb. A variable compliance matrix eases the transition between "go" and "no-go" areas, connecting the counters, the lacing system, and the flexible hinges, and provides four-way stretch over the "no-go" areas, allowing the free movement of the soft tissue beneath.

A socket for engaging a residual limb includes a plurality of hard counters, each configured to engage the residual limb at defined "go points" specific to each level of amputation or individual anatomy. The go points can bear pressure without discomfort or impeding range of motion. The counters are further configured to avoid contact with identified "no go" points where excess tissue may inhibit motion or experience irritation upon movement and which include one or more contoured pads to more effectively engage the bony prominences of the limb without inhibiting motion. A chassis from which each of the counters may flexibly depend connects the residual limb mechanically to a limb extension. A lacing system alternately intersects the counters and terminates in a tensioning reel. Rotation of the tensioning reel in a first direction will draw the laces over each of the counters such that the tensioned laces will draw counters together to engage the residual limb.

BRIEF DESCRIPTION OF THE DRAWINGS

The various advantages of the embodiments will become apparent to one skilled in the art by reading the following specification and appended claims, and by referencing the following drawings, in which:

FIGS. 2A and 2B are a pair of radiographic images of a limb in engagement with a prior art monolithic Meunster Socket under load and no load, respectively;

FIGS. 3A and 3B are a pair of radiographic images of a limb in engagement with a monolithic TRAC Socket under load and no load, respectively;

depicted in polka dots) in a trans-radial embodiment of the invention; A counter may be self-reinforcing, or resist a direction of motion relative to the limb with increased loading in one or more directions. A counter can also be mutually reinforcing, or resist motion through its mechanical connection with the sock and other counters through a lacing system.

Figure 5A:
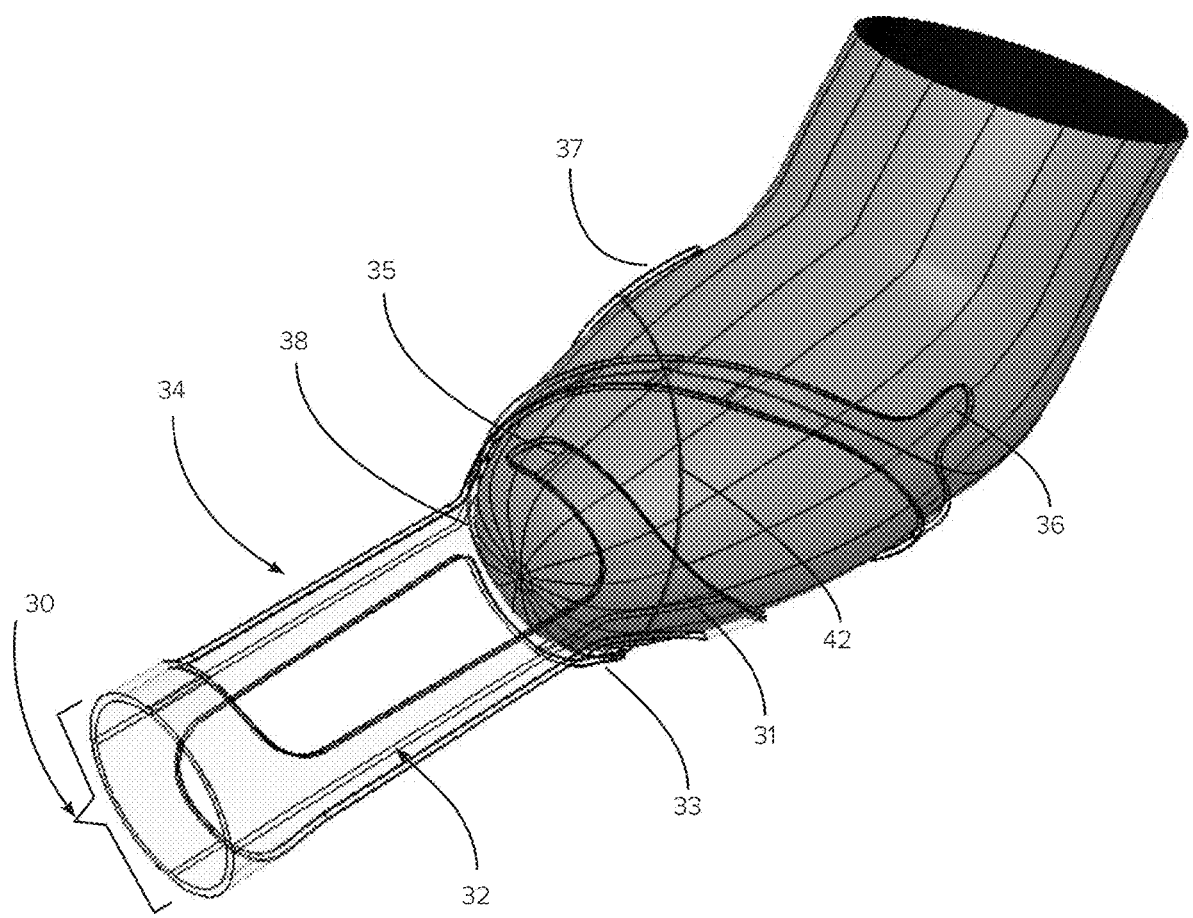
Figure 5B:
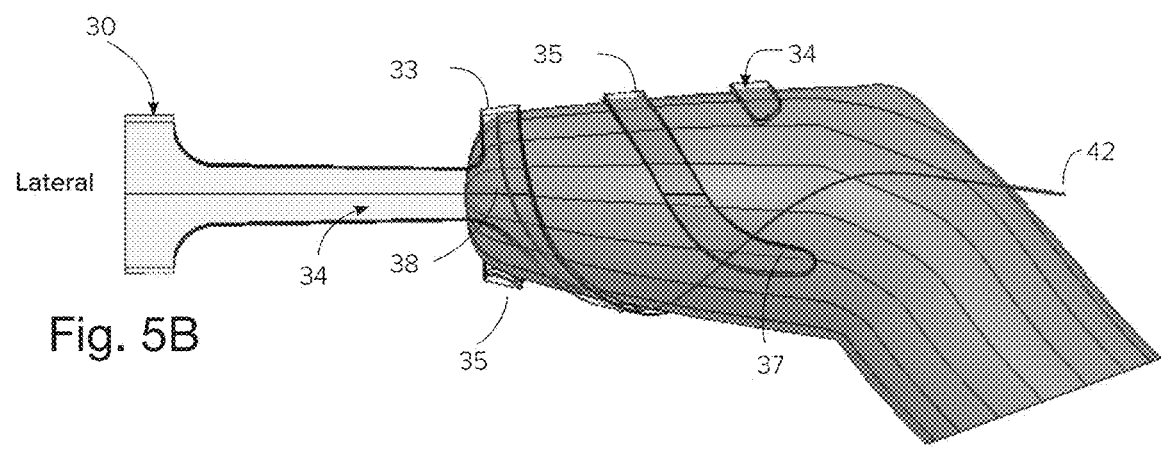
Figure 5C:
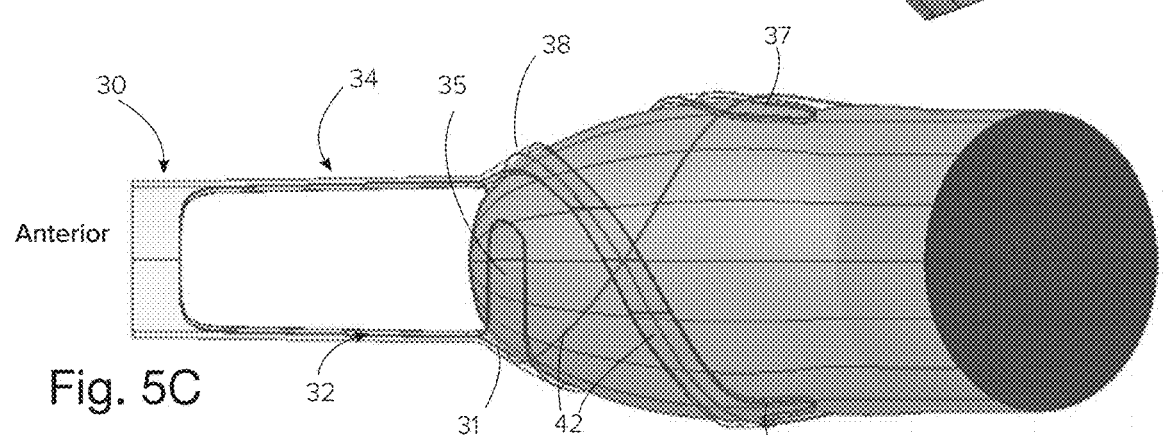
Figure 5D:
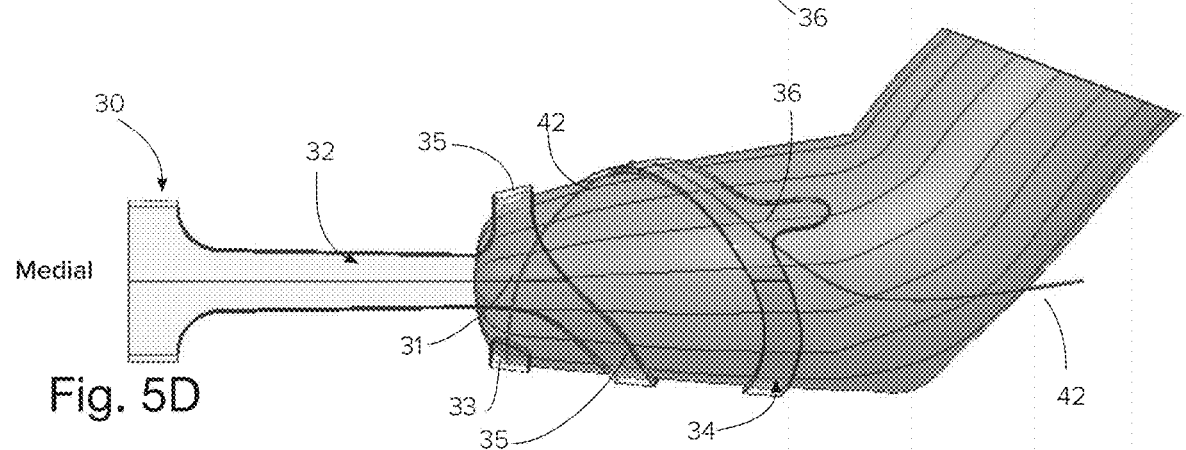
Figure 5E:
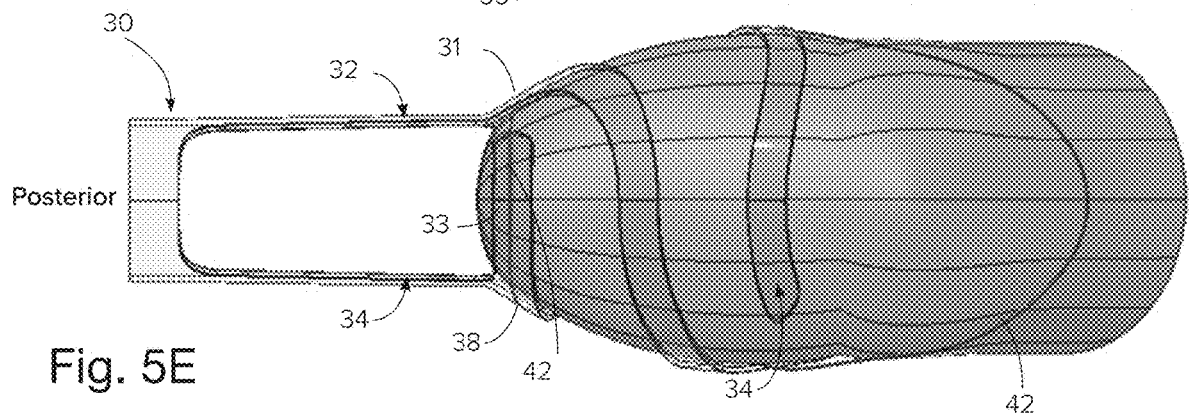
Figure 6A:
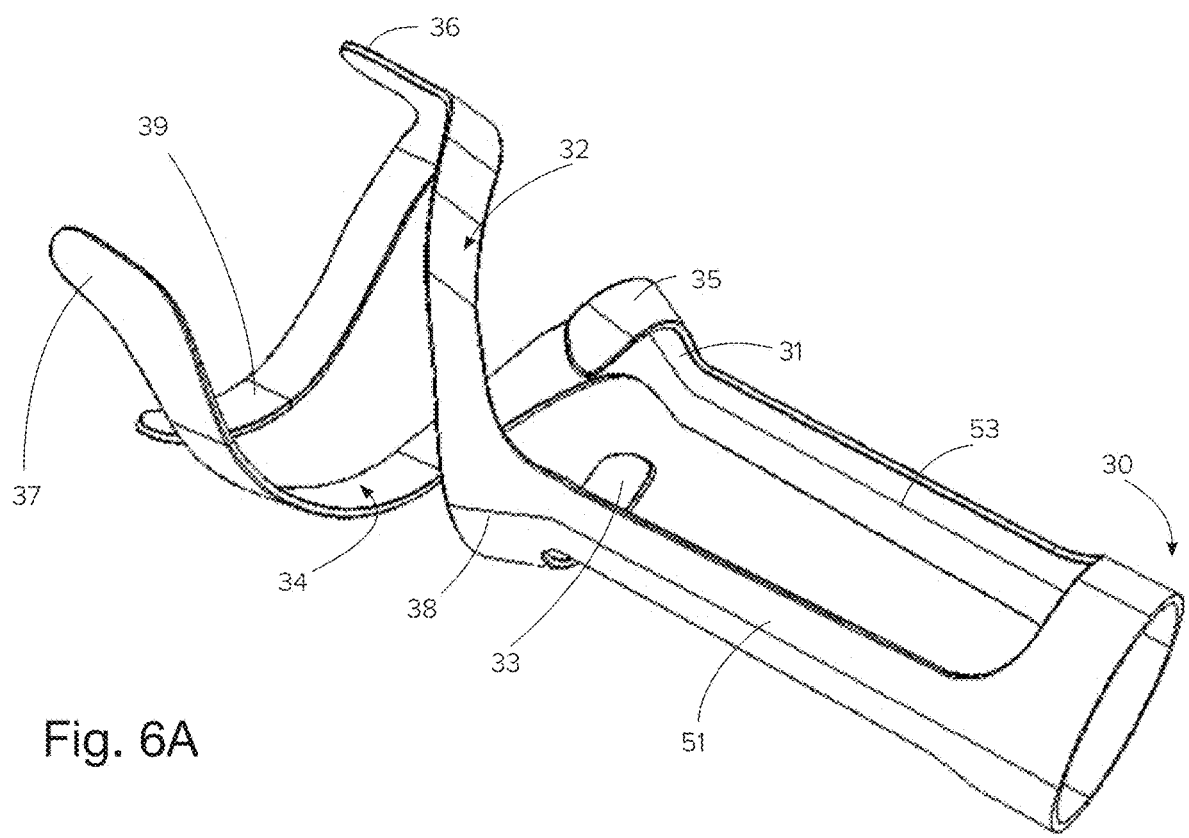
Figure 6B:
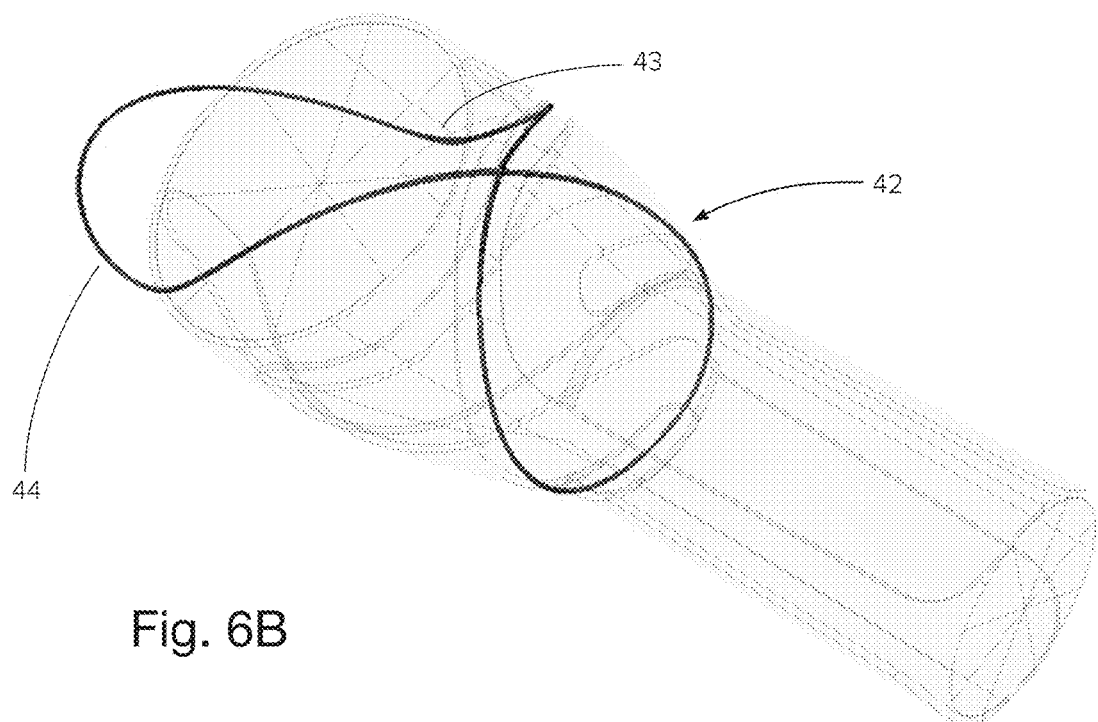
Figure 8A:
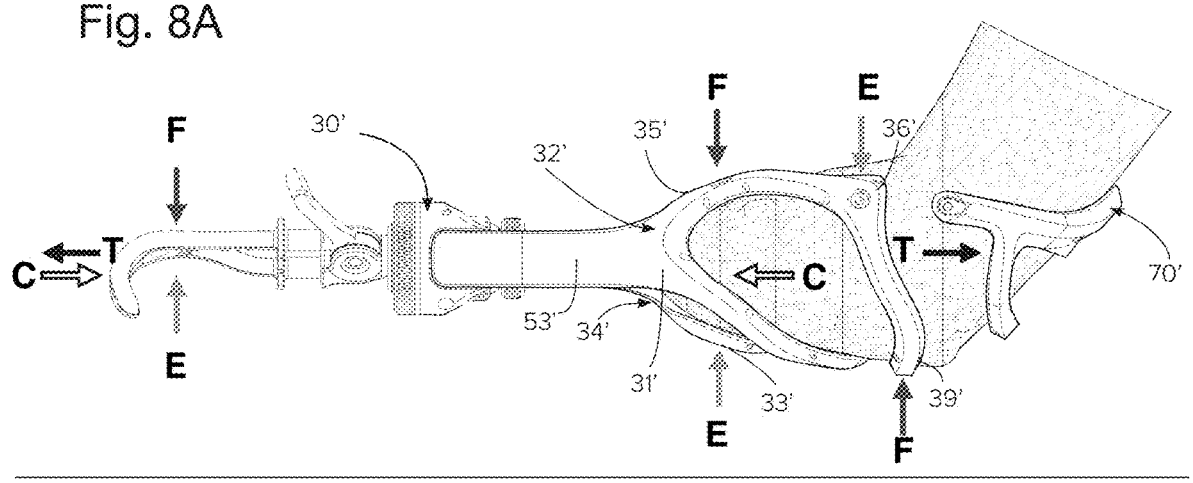
Figure 8B:
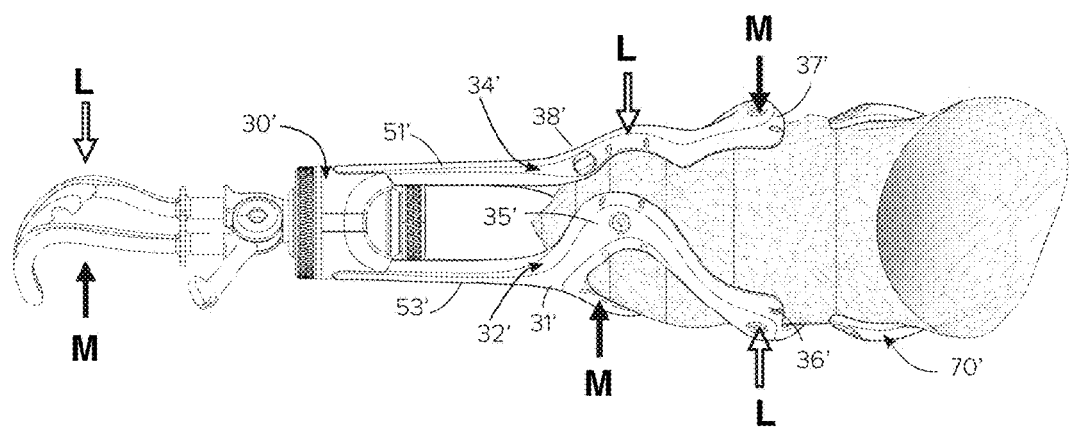
Figure 9:
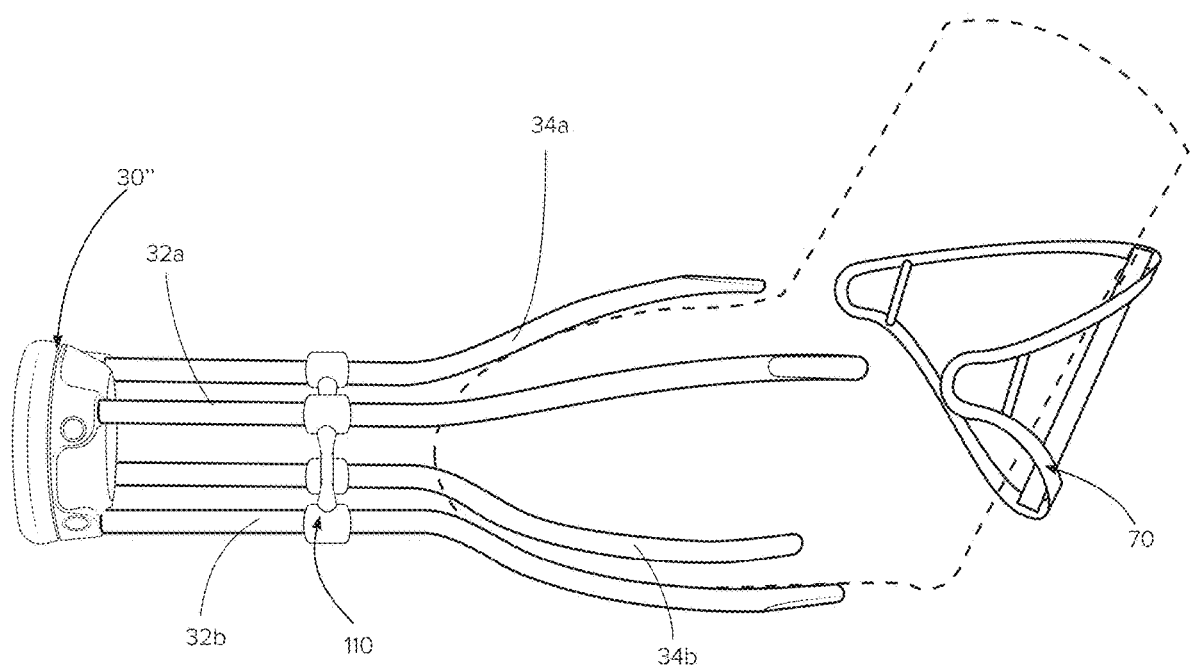
Figures 10A, 10B:
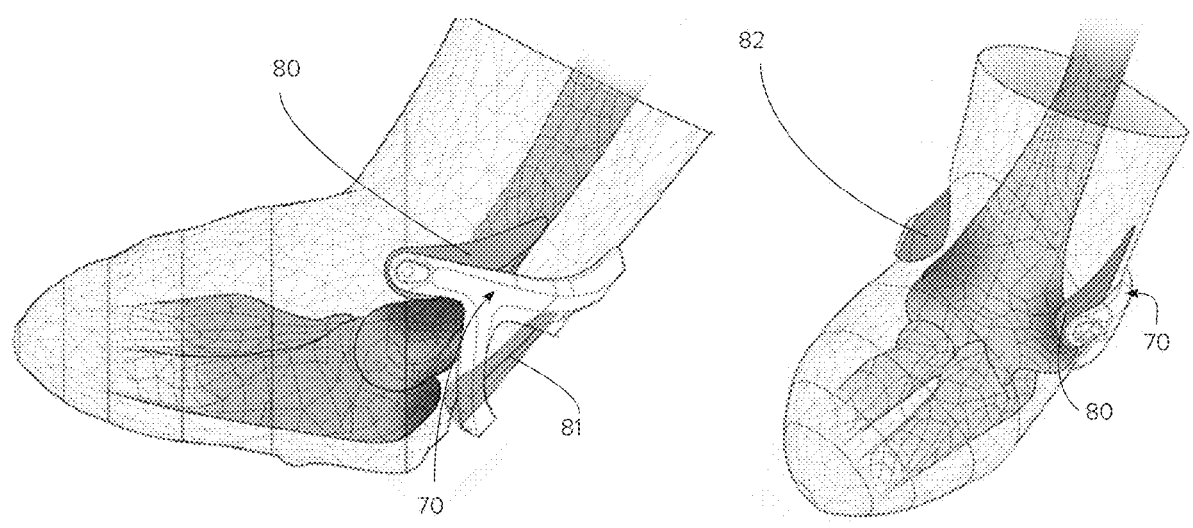
Figure 11A:
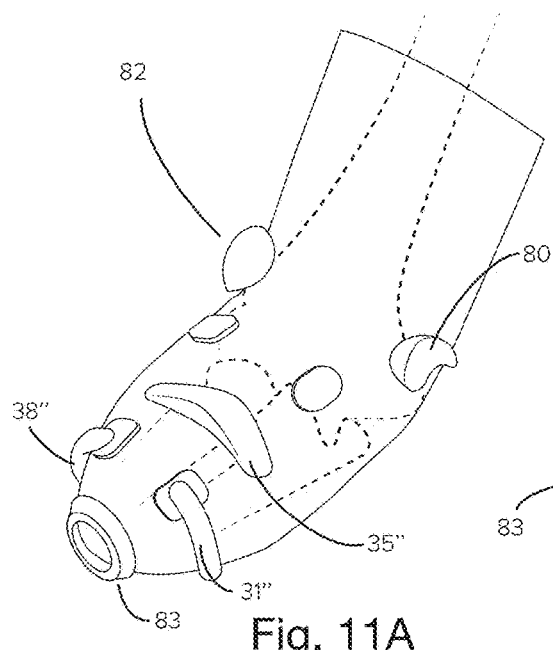
Figure 11B:
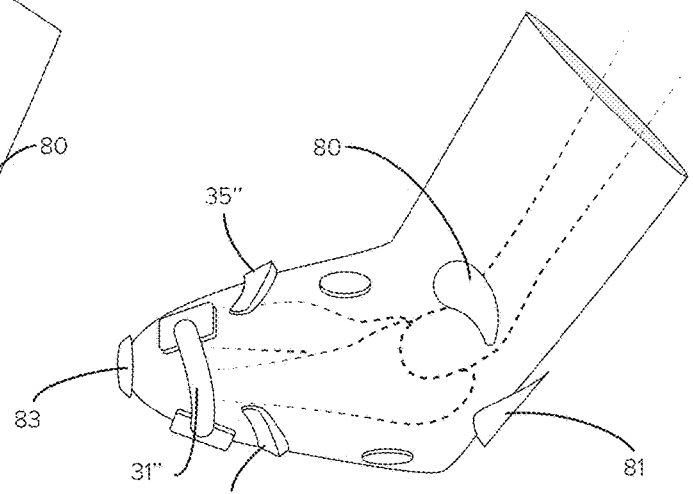
Figures 12A, 12B, 12C, 12D:
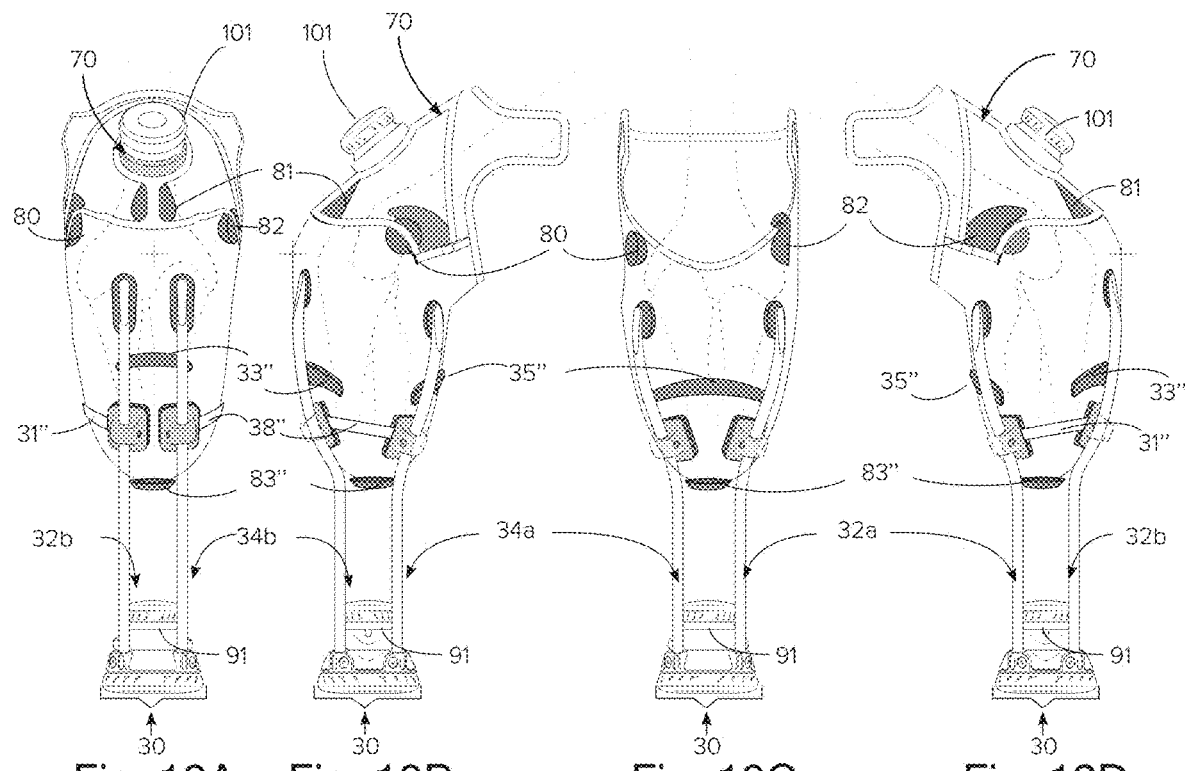
Figures 13A, 13B, 13C:
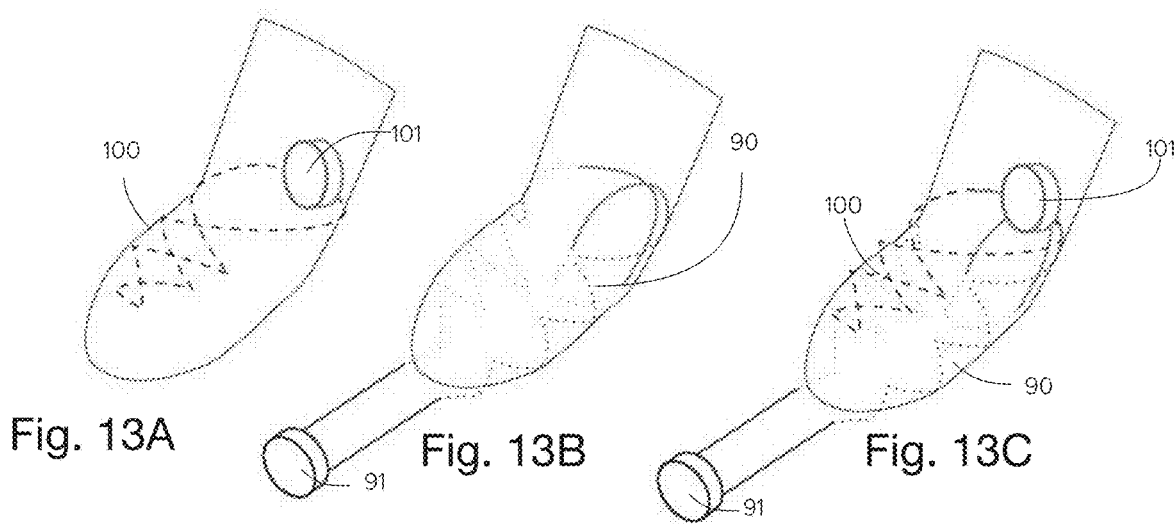
Figure 14:
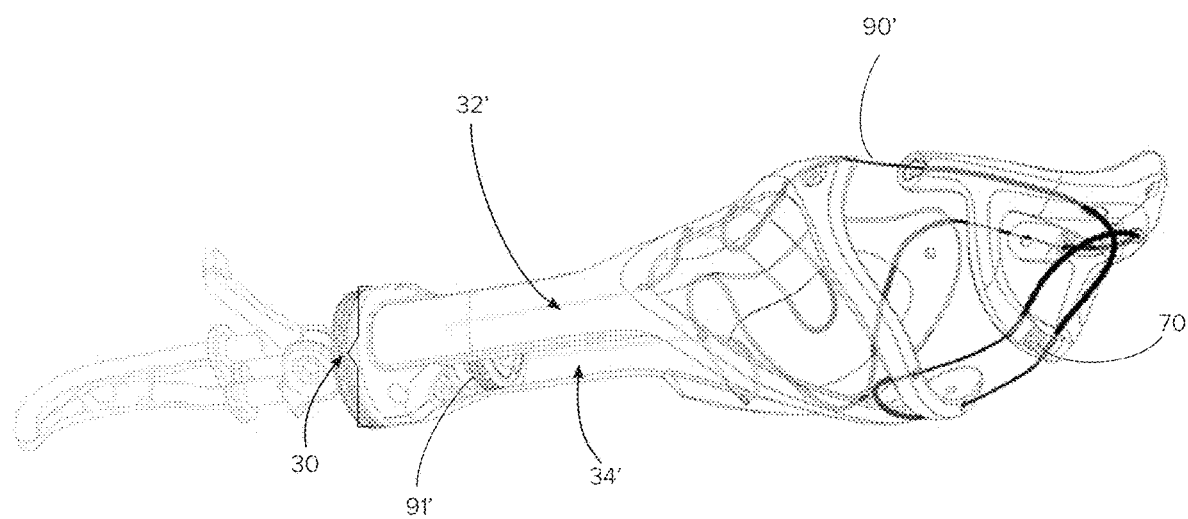
Figure 15A:
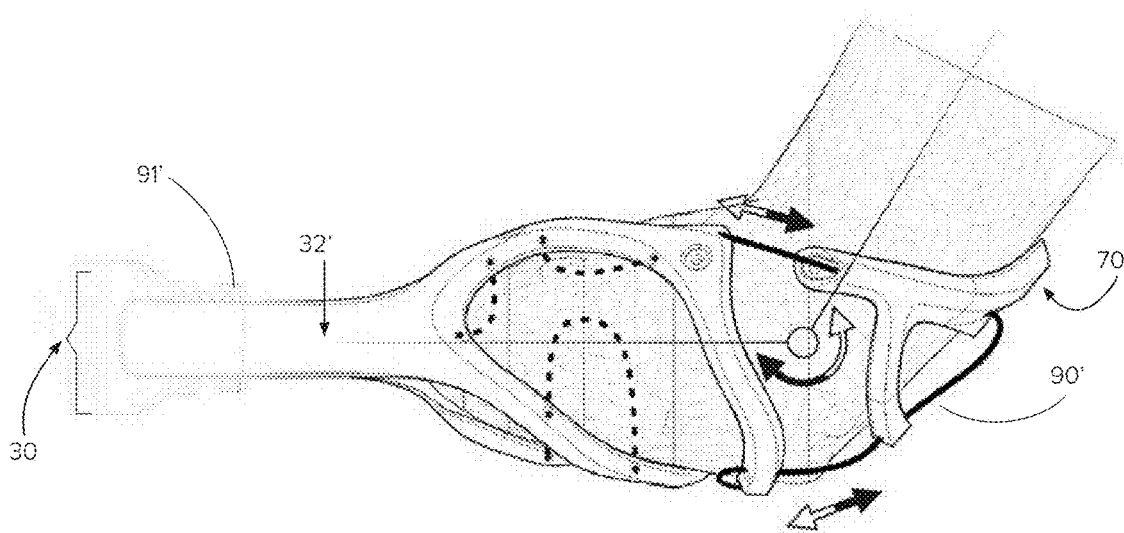
Figure 15B:
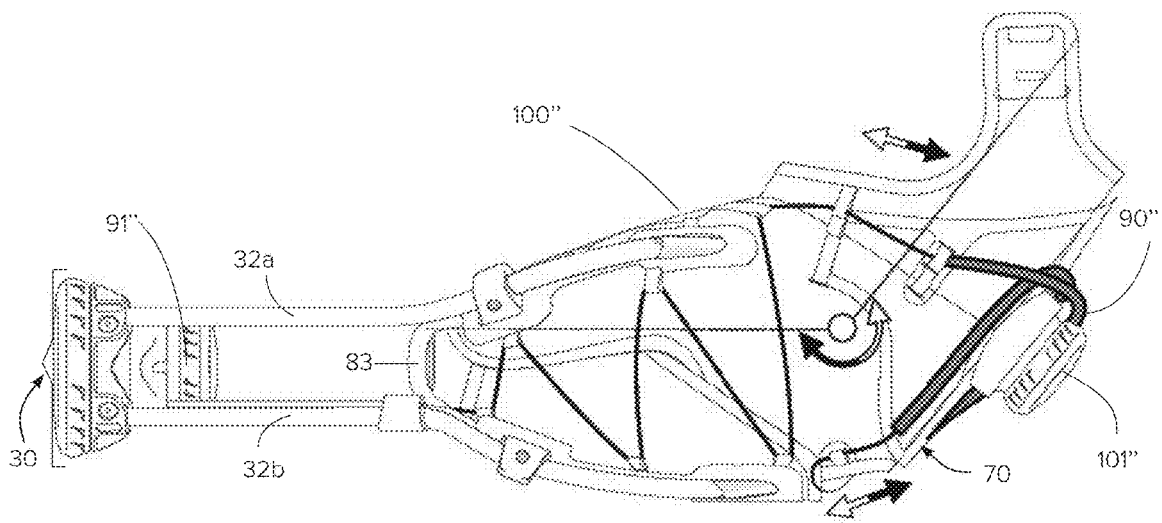

FIG. 5A is a rendered illustration in perspective view depicting a right trans-radial embodiment of a helical socket with a limb a relative placement of the medial and lateral counters, as well as the routing of the balancing lace system through and around the limb and counters in the exemplary embodiment;

FIG. 5B is a rendered illustration in right side medial view depicting the right trans-radial embodiment of the helical socket with limb a relative placement of the medial and lateral counters, and the routing of the balancing lace system through and around the limb and counters;

FIG. 5C is a rendered illustration in right side lateral view depicting the right trans-radial embodiment of the helical socket with limb the relative placement of the medial and lateral counters, and the routing of the balancing lace system through and around the limb and counters;

FIG. 5D is a rendered illustration in right side anterior view depicting the right trans-radial embodiment of the helical socket with limb the relative placement of the medial and lateral counters, and the routing of the balancing lace system through and around the limb and counters;

FIG. 5E is a rendered illustration in right side posterior view depicting the right trans-radial embodiment of the helical socket with limb right depicting the relative placement of the medial and lateral counters and the routing of the balancing lace system through and around the limb and counters;

FIG. 6A is a rendered illustration in a perspective view depicting the right trans-radial embodiment of the helical socket counters without limb, demonstrating the medial and lateral counters' relative positions, stiffly encircling the arm;

FIG. 6B is a rendered illustration in a lateral view depicting the right trans-radial embodiment of the helical socket counters without limb, depicting an exemplary lace to draw the the medial and lateral counters' into engagement with the residual limb from relative positions, stiffly encircling the limb;

FIGS. 7A and 7B are, respectively, a side view and a plan view of the chassis showing the medial and lateral counters and forces that work the counters;

FIG. 8A is a rendered illustration showing showing forces acting on the nonlimiting example of the right trans-radial socket with limb extension;

FIG. 8B is a rendered illustration showing showing forces acting on the nonlimiting example of the right trans-radial socket with limb extension;

FIG. 9 depicts a four rod counters (Medial and Lateral) and interior contoured supports of the soft socket;

FIGS. 10A and 10B are a pair of rendered medial view illustrations showing the interaction of the stiff external counter and cuff and contoured internal supports with and the epicondyles of the humerus when the limb is engaged in the right trans-radial embodiment of the internally cabled elbow counter and supracondylar cuff demonstrating bone interaction;

FIGS. 11A and 11B are perspective views of an embodiment of the invention employing lacing and rigid structure sutures to perform lacing functions;

FIGS. 12A, 12B, 12C and 12D are a bottom, left, top and right side illustrations showing the interaction of the stiff external counter and cuff and contoured internal supports with and the epicondyles of the humerus when the limb is engaged in the right trans-radial embodiment of the internally cabled elbow counter and supracondylar cuff demonstrating bone interaction;

FIG. 13, depicts the lacing system including laces and a tensioning reel;

FIG. 14 is an illustration of medial and lateral counters, together with the elbow counter of a soft socket in the right trans-radial embodiment demonstrating lace routing to draw counters together in engagement to a limb at the elbow;

FIGS. 15A, and 15B are a series of rendered illustrations developing the soft socket lacing system layout showing A) the Balanced Hinge Lacing System and B) the top lace system, each in isolation FIG. 16 demonstrates the effects of elbow flexion as a that flexion varies tension based upon lacing position in showing the movement of the elbow at the neutral axis, and the balancing action of the flexible hinges in the right trans-radial embodiment of the internally cabled socket, with specific depiction of the axis of rotation and balancing flexible hinges;

FIGS. 17A and 17B are lateral and plan views, respectively, of the soft socket with all components showing the mutually supporting function of the four medial and lateral counter rods and the Top Lace and Balanced Hinge Lacing System.

DETAILED DESCRIPTION OF THE INVENTION

Figures 1A, 1B:
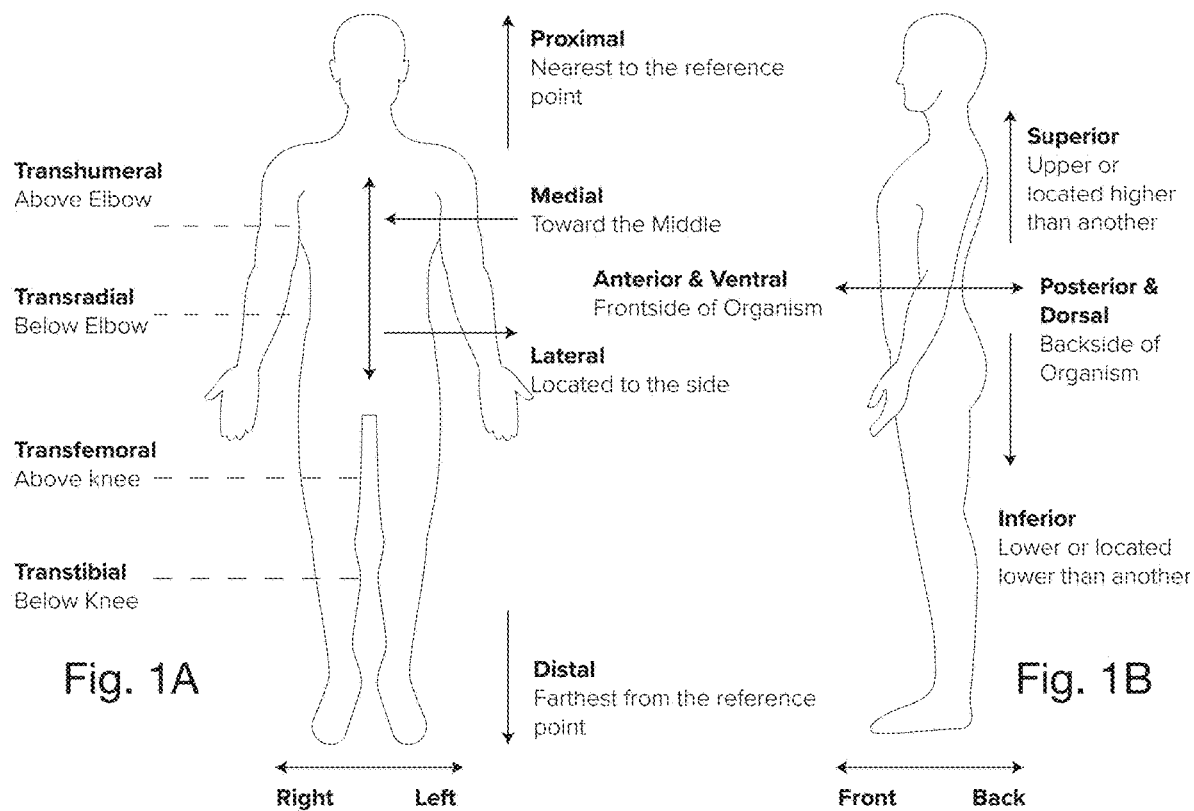
FIG. 1: Reference atlas of human body in Standard Anatomical Form (SAF) position with view directions including: medial and lateral, proximal and distal, anterior and posterior.
Figure 4A:
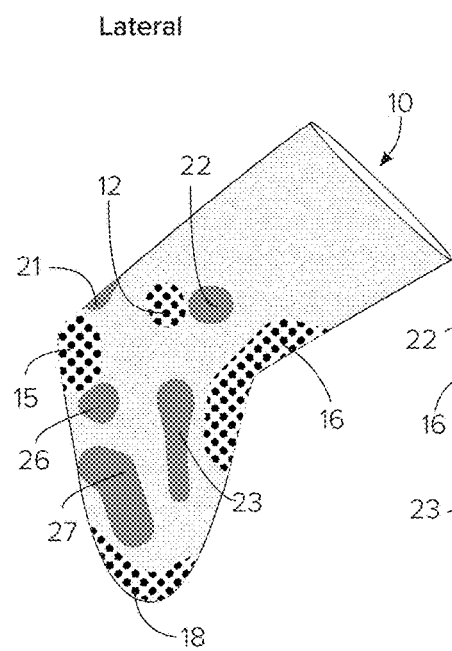
FIGS. 4A, 4B, 4C and 4D are a series of rendered illustrations of a nonlimiting exemplary figure depicting appropriate anatomical locations for counter pressure to be applied ("go" depicted as shaded) and avoided ("no-go"
Figure 4B:
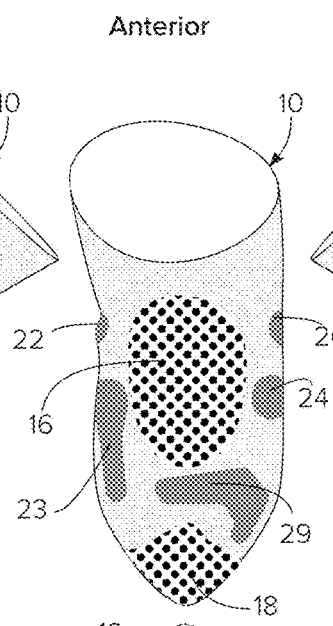
Figure 4C:
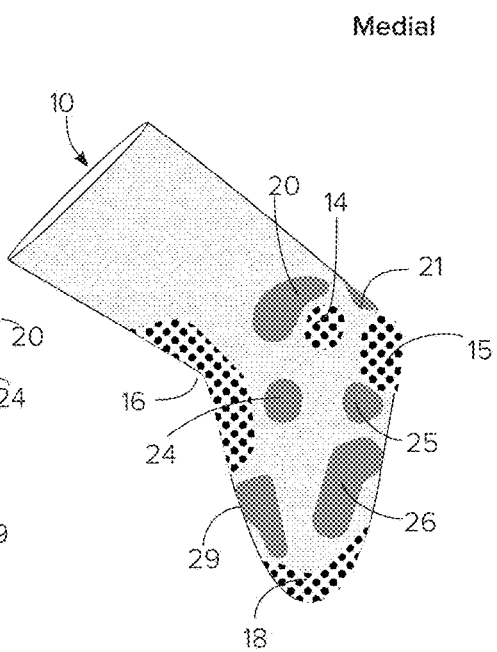
Figure 4D:
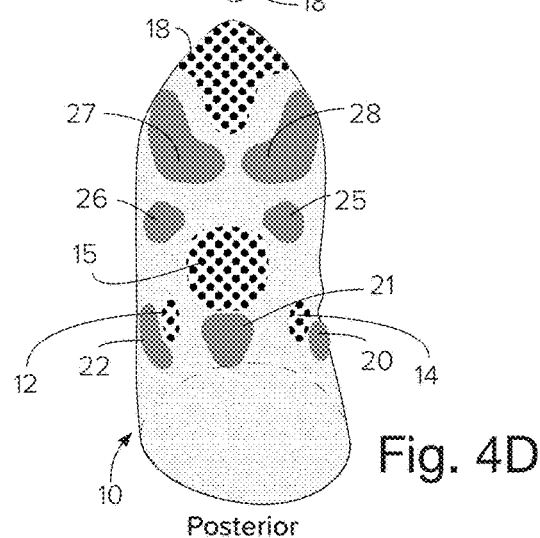

Throughout this application, certain terms such as "distal" and "medial" have accepted medical meanings. To assist in understanding the teaching of this Specification, the applicant provides FIG. 1, a reference atlas of human body in Standard Anatomical Form (SAF) position with view directions including the terms "medial" and "lateral"; "proximal" and "distal"; and "anterior" and "posterior". To further aid in discussion of various embodiments of the invention, the names for the locations of different levels of amputation have been identified, including "transradial," "transhumeral," "transtibial," and "transfemoral," are identified on the same figure.

To express the issues presented by conventional prostheses, the application provides FIGS. 2A and 2B. FIGS. 2A and 2B are a pair of radiographic images depicting a prior art monolithic Meunster Socket both under load and in a no load state, respectively while FIGS. 3A and 3B are a pair of radiographic images of a limb in engagement with a monolithic TRAC Socket under load and no load, respectively. The angles shown indicate the quantum of movement of the residual arm bones allowed or tolerated within the inside of the socket under load. This tolerated movement is known as the "slop" in the socket fitting, which is somewhat more than might occur in the TRAC socket. The traditional monolithic TRAC Socket as shown in FIGS. 3A and 3B similarly show angles that indicate this same "slop" in the socket fitting, which is somewhat less than the Meunster socket. These prior art illustrations are from a study by Miguelez, J. M., et al. published in 2003 addressing this issue.

FIGS. 4A, 4B, 4C and 4D are a series of rendered illustrations of residual limb including depicting the appropriate anatomical locations for counter pressure to be applied ("go" depicted as shaded) and avoided ("no-go" depicted in polka dots). The advantages of recognizing these two types of regions as exploited in a nonlimiting exemplary trans-radial embodiment of the invention. As stated above, the term "counter" will be used herein to describe batten-like structures that rest against "go" surfaces avoiding contact with "no-go" surfaces. A counter according to the invention may, optionally, be referred to as "self-reinforcing" or "self-supporting," meaning that it may be configured to resist a motion relative to the limb wherein movement increases loading in one or another direction. In some examples, a self-supporting counter may operate as a statically loaded beam, with an applied force and reaction forces that 'counter' the applied force. A counter can also be termed "mutually reinforcing" meaning that it is configured to resist motion through its mechanical connection through a removable sock that resides within the socket to the counters the socket comprises. Counters may be configured to maintain consistent attachment and comfort of the prosthetic socket onto the residual limb in any given movement of the terminal device. Engagement between the residual limb and the socket counters is controlled through tension applied by a lacing system described herein.

As shown herein, the residual limb 10 has a lateral aspect on which the lateral epicondyle No-Go zone 12 is located, similarly a medial epicondyle No-Go zone is place in opposed relation on the residual limb. An olecranon No-Go zone 15 is on the posterior of the limb and in opposed relation a cubital fold No-Go zone is also defined. A distal tip No-Go zone is shown. A medial epicondyle support is a Go zone as is located at a olecranon fossa support 21. On one side, a lateral epicondyle support, Go zone and a lateral anterior proximal support are also readily located. On the opposing side, the medial anterior proximal Support 24, the medial posterior proximal support 25, the lateral posterior proximal support 26 are located. Returning, the to opposite side, a lateral posterior distal support 27 with its opposed medial posterior distal support 28. On the upper surface of the residual limb a distal anterior support 29 is defined.

As is readily apparent to those having ordinary skill in the art in viewing the preceding, appropriate anatomical locations for counter pressure to be applied ("go") and avoided ("no-go") in a nonlimiting transradial embodiment of the invention are exploited to anchor the inventive device and to receive supportive or driving pressures from the residual limb in a loaded state. In general, "go" areas are selected as those that can bear pressure without discomfort or impeding range of motion. "Go" areas give access to the skeletal structure without much excess tissue to intervene in mechanical connection or to experience irritation upon movement of the involved joint. It is displacement of the intervening tissue that could create the noted undesired movement or "slop" in such a fitting of the socket to the residual limb. Conversely, "no-go" areas must not be relied upon for such supportive or driving engagement because routing of nerves, excess soft tissue, or significant volume of tissue or surface area stretching or movement consequent to rotation of the joint would result in the loss of range of motion or discomfort. By way of non-limiting example, the cubital fold (also known as the "cubital fossa", "chelidon", or "elbow pit" and is the triangular area on the anterior view of the elbow) is a "no-go" area, which, if covered by hard socket or even non-stretch fabric can significantly limit range of motion due to the volume change on flexion. By way of further non-limiting example, the skin surface area around the olecranon (the large, thick, curved bony eminence of the ulna, a long bone in the forearm that projects behind the elbow) stretches so significantly on flexion that even non-stretch fabric can severely limit range of motion. Both of these "no-go" areas are notable as intersecting the plane of rotation for the elbow joint. Other "no-go" areas include areas where nerves are close to the skin, and the distal tip of the residuum, which can be sensitive for lack of a bursa. "Go" areas are generally where bones are close to the surface of the skin and weight can be borne without significant discomfort.

To exploit the inventive concept of the socket, helical counters can be configured and have proven to be capable of connecting "go" areas without significant incursion into identified "no-go" areas. Due to the anatomic structure of the limb, the distribution of "go" areas across the surface of the limb allows configured helical counters to rest on the limb's surface without irritating identified "no-go" areas. Helices can be configured for each of the four limbs and suitably chosen to exploit such of the residual limb as remains without incursion into "no-go" areas. These defined helices are readily determined by the study of dimensions of the residual limb and to the extent that such counters must be constructed, they might either be constructed in standardized sizes for selection to "tailor" a socket for an amputee, or to be cut from selected material having specifically selected compliance by computer-controlled devices of a group or devices described as "CNC machining", an exemplary group which includes such as routers, water jets, laser cutters, and die cutters. Thus, in a fully customized construction, imagery of the residual limb is analyzed to identify "go" and "no-go" areas and, in at least one embodiment, a computer is used to form helices that will overlay and engage "go" areas and will minimally incur onto "no-go" areas. Nothing in this discourse, however, requires computer analysis of the imagery to suitably form the helical counters to practice the invention. A person with suitable knowledge of anatomy and function can readily measure a residual limb and form a serviceable counter that will overlay and engage "go" areas and will minimally incur onto "no-go" areas in accord with embodiments of this invention.

To demonstrate the necessary formation of counters along the helices in accord with the criterion that the counter will rest on "go" areas without irritating "no-go" tissue areas, FIGS. 5A through 5E display a series of rendered illustrations depicting a nonlimiting example of the right transradial embodiment of a helical socket with a residual limb, the illustrations depict a relative placement of the medial and lateral counters, as well as the routing of a balancing lace system that will be further described below but, for displaying an exemplary lacing through and around the limb and connecting counters in the this non-limiting exemplary embodiment.

The medial and lateral helical counters form together a double helix in which each counter forms a self-reinforcing resistance to at least two directions of external loading. The helical counters in FIG. 5 are right-handed moving distally. Both right and left arm embodiments could be composed of either a left or right-handed double helix, which, by definition, must not cross, staying generally equidistant. Reviewing the structure of the socket 10, the chassis 30 in this helical counter embodiment from which extent the medial support 31, the medial counter 32 joining at the posterior distal support 33. The lateral counter 34 also extends from the chassis 30 in opposed relation to the the medial counter 32. From the medial counter, to exploit a go zone thereby, a anterior distal support 35 extends. For similar reasons a medial epicondral support 36 extends from lateral counter 34. The medial counter 32 extends to a radial fossal support 37 while a lateral support 38 extends from the lateral counter Beginning with the most proximal "go" area of the lateral anterior side of the transradial forearm, specifically the radial fossa, which is slightly superior to the lateral epicondyle and anterior to the humeroradial joint, we will first construct the right-handed helical medial counter. Moving distally, the counter briefly follows the radius, then moving laterally over the radius and around the posterior of the ulna, and then anteriorly again to the medial side of the ulna, continuing to the anterior side of the ulna. Having reached the most distal "go" area, avoiding the distal tip, which, lacking a bursa is often sensitive, we have completed our helical turn around the residual limb.

Because the residual limb or "residuum" is part of the structure, the bones and tissue keep the helix from twisting and collapsing. This does not hold distal to the residual limb, so the helix must be terminated, and a forearm structure or chassis will in the assembly resist forces in multiple directions as constructed. In this embodiment, a forearm beam is attached prior to the terminated helix on the medial side, oriented to be strongest in flexion.

The completed medial counter is shown with the limb in the socket in FIGS. 5A and 5B, and contains a radial fossal support, follows the radius and then the posterior side of the ulna, to the medial support, engenders the medial forearm beam, and terminates in the anterior distal support.

The medial counter is self-supporting and resists isometric extension with reaction forces at the radial fossal support and along the length of posterior of the ulna as it crosses. The medial counter resists isometric internal rotation again at the radial fossal support and at the medial support where the counter engenders the medial forearm beam, oriented to resist extension. This embodiment can be lengthened to accommodate any length of residual limb, with the radial fossal support and anterior distal support marking the length of the residual forearm, and is more effective with greater length of long bone contact. The anterior distal support reinforces the anterior support of the lateral counter and offers redundant mutual support.

The right-handed lateral counter is similarly constructed, beginning with the most proximal ulnar bursal support, wrapping medially and anteriorly, extending the medial epicondyle support (avoiding the olecranon), continuing laterally and avoiding the cubital fold of the anterior elbow, moving to the lateral side of the forearm and terminating at the posterior distal support after engendering the lateral forearm beam. As the medial counter does, the lateral helical counter connects all of the "go" areas while avoiding the "no-go" areas, including the olecranon, the tip of the medial epicondyle, the cubital fold and the distal tip of the residual limb.

The right-handed lateral counter is self-supporting and resists isometric flexion with reaction forces at the ulnar bursal support and along the length of the radius as it crosses and wraps to the lateral side. It resists isometric external rotation with reaction forces at the medial support and at the medial epicondyle support (avoiding the tip of the epicondyle). The lateral helical counter can be similarly lengthened to match residual limb length and is more effective with greater length of long bone contact. The posterior distal support reinforces the posterior support of the medial counter, and offers redundant mutual support.

FIG. 6A is a rendered illustration in a perspective view depicting the right trans-radial embodiment of the helical socket counters without limb, demonstrating the medial and lateral counters' relative positions, stiffly encircling the arm. FIG. 6B is a rendered illustration in a lateral view depicting the right trans-radial embodiment of the helical socket counters without limb, depicting an exemplary lace to draw the the medial and lateral counters' into engagement with the residual limb from relative positions, stiffly encircling the limb. Together these FIG. 6 demonstrate an alternative embodiment of medial and lateral counters connects the same "go" and "no-go" areas as the helical counters, but instead of wrapping all the way over the arm and engendering the forearm beams on the opposite side from where they began, the "clamping counters" simply continue on the same side, each forming a loop that closes and engenders the forearm beams.

The lateral clamping counter begins at the same location as the medial helical counter—at the radial fossa. The counter bifurcates, skirting the lateral side of the cubital fold anteriorly and moving laterally over the radius and medially to create the posterior distal support, and then reunites, engendering the lateral forearm beam.

The lateral clamping counter is self-supporting only in resistance to isometric extension, and requires lacing to support lateral forces. FIGS. 7A and 7B are, respectively, a side view and a plan view of the chassis showing the medial and lateral counters and forces that work the counters. As shown the right trans-radial embodiment of the internally cabled socket of the right trans-radial embodiment depicting external and reaction force locations, showing each of the external forces generated by isometric flexion (F), extension (E), compression (C), and tension (T), as well as the locations of the reaction forces generated internal to the socket in response;

FIG. 8A is a rendered illustration showing showing forces acting on the nonlimiting example of the right trans-radial socket with limb extension; and FIG. 8B is a rendered illustration showing showing forces acting on the nonlimiting example of the right trans-radial socket with limb extension. The medial clamping counter begins at the same location as the lateral helical counter—at the ulnar bursa. Skirting the olecranon in both directions, creating a loop, the counter moves medially and anteriorly, with an extension to reach above the medial epicondyle. The counter continues, skirting the cubital fold and then creating the anterior distal support. The other direction of the loop crosses over to the lateral side of the ulna, and then returns to the medial side, meeting the other end and creating the medial forearm beam. An elbow counter 70 secures the residual limb in the socket. The medial clamping counter is self-supporting in resisting isometric flexion, and to a lesser degree isometric internal rotation, because it crosses to the lateral posterior side of the ulna.

FIG. 9 depicts these four rod counters (Medial and Lateral) and interior contoured supports of the soft socket supported by a brace 110. This third embodiment of the forearm counters consists of four structurally independent counters rather than two: anterior and posterior lateral counters, and anterior and posterior medial counters. In contrast to the previous counter embodiments, none of these counters is self-supporting, and they are attached to each other only at the wrist, as shown in FIG. 9. They may be additionally stiffened by a brace distal to the residual limb that can me made of metal, plastic or of elastomeric material to provide damping as well as additional stiffness. These counters will rely more heavily than the others on padding, lacing, and matrix stiffening to achieve mutual support and to minimize undesired movement, but the resulting socket will also be less constraining than those with stiffer and self-supporting counter designs.

The simplest prior art elbow counter 70 is the body-powered backplate, which is usually made of stiff leather or fiberboard, and attached to the forearm with flexible or metal hinges. The backplate allows the user to push the elbow against the control cable to actuate a body powered terminal device. An embodiment of the elbow counter in this invention includes a stiff metal or plastic counter, mounting for a reel for one or more lacing systems, and routing for the control cable, as shown in FIGS. 9 and 10, and accompanied by internal contoured padding. Another embodiment of the elbow counter includes only textile and sheet glue stiffener, accompanied by internal contoured padding.

To further exploit the relevant go zones a medial epicondyle support pad 80 might, optionally be used. Likewise an olecranon support pad 81, a lateral epicondyle support pad 82, a posterior medial rod counter 83 and a posterior lateral rod counter 84 may be used individually or in concert to perform or enhance the function of the elbow counter 70. Where the forearm and elbow counters interact with the "go" areas of the limb, their function in engaging the bony prominences may be enhanced with the use of contoured pads with stiff cores. In the case of the anterior and posterior distal supports, for example, when the limb is loaded in either flexion or extension, the distil tip of the limb will begin to shift, as shown in the radiographic images in FIGS. 2 and 3. In order to prevent this from leading to significant uncomfortable movement of the limb against the socket, or pressure preventing range of motion, a contoured pad is placed proximally to the distal tip at each of these locations. With something padded to push against, the limb is more immediately and comfortably engaged without placing painful pressure on the distal tip of the limb. Additional pads help cushion the limb in any movement against any part of a counter.

In the case of the elbow, significant tensile loads can be borne by the processes proximal to the medial and lateral epicondyles, as well as by the olecranon fossa. The epicondyles are consistently offset slightly and differently shaped, and contoured stiff pads can be placed inside the elbow counter, comprising the medial and lateral epicondyle supports. A similar stiff olecranon fossa pad can lock the elbow counter into the humerus strongly enough to support significant weight, even at full extension.

Once a specific shape for each of the counters and corresponding contoured pads is determined a socket and structure may be formed for either of body-powered or robotic prostheses in accord with the instant invention. FIGS. 6A through 6C are a series of rendered illustrations depicting the right trans-radial embodiment of the helical socket counters without the presence of the limb. Such would be an exemplary structure for a chassis to a prosthesis in accord with the instant invention, the figures demonstrating the medial and lateral counters' relative positions, stiffly encircling the residual limb. The chassis is, preferably, a monolithic structure as shown to provide rigidity along its length while the helical counters are configured to compliantly engage the residual limb.

As earlier described, the counters are drawn into engagement with the residual limb by stricture of lacing under tension. FIGS. 11A and 11B are perspective views of an embodiment of the invention employing lacing and rigid structure sutures to perform lacing functions. Building out on the exploitation of the rigid lacing bridges working in concert with various of the support pads 80-84, a complete socket is formed as depicted in FIGS. 12A, 12B, 12C and 12D are a bottom, left, top and right side illustrations showing the interaction of the stiff external counter and cuff and contoured internal supports with and the epicondyles of the humerus when the limb is engaged in the right trans-radial embodiment of the internally cabled elbow counter and supracondylar cuff demonstrating bone interaction. The lace fixation helix is facilitated by assemblies and systems to allow the use of small-diameter, low-friction lace material. The lace fixation assemblies and systems of the present disclosure may further provide a convenient means to store excess lace after tightening while allowing quick and easy release and refastening of the fixation after suitable tension adjustment. The lace fixation assemblies and systems of the present disclosure may further be of a design and material such as plastic or other synthetic material that is economical to produce and to incorporate into existing manufacturing methods.

The lacing system includes or comprises fixation members coupled to one or more of the counters above-described and because the fixation members are arranged to define the fixation helix that corresponds, in general shape, to the helix of the counter. The fixation members define a fixation lumen that at least one of the counters defines and the lumen follows the surface of the counter such that tension along this fixation helix will not result in significant engagement with the residual limb. The counter or counters define at least one entry aperture and an exit aperture with the fixation lumen extending therebetween.

In embodiments of the invention, the fixation member may, optionally, include a tensioning member such as a tensioning reel 101. In one embodiment the tensioning member comprises a spool with a fixation post. In this example, the fixation member may be rigidly fastened to the counter containing the lumen. The lumen may define a passage, a cavity, a tube structure, or the like. Further, the exemplary spool may include or comprise a flanged cylinder whereby a cable may be wound around the spool as it rotates on the post. Other embodiments are possible.

The lacing system further includes or comprises a tension helix having at least one intermediate portion slidably disposed along the tension helix and affixed to the fixation counter, intermediate portion defining at least one tension lumen such that a proximal portion of the cable through the tension lumen is positioned to a proximal side of the fixation counter and a distal portion of the cable tension passing through the tension lumen is positioned on a distal side of the fixation counter such that a length of the proximal portion and a length of the distal portion is adjustable via sliding of the cable within the tension lumen. In this example, the tension cable may include or comprise a lace or lacing that has a lace diameter. The cable through the tension lumen may generally be laced to the fixation member, and a length of the cable protruding or exiting from the tension lumen may be adjusted as desired. Other embodiments are possible.

The lacing system may further include or comprise a plurality of guide members coupled to the fixation counter to guide the proximal portion of the cable along through the tension lumen to draw the fixation counter toward the remaining counter or counters. In this example, the cable may generally be laced to each of the plurality of guide members.

Other embodiments are possible such as that shown in FIG. 13. FIG. 13 depicts the lacing system including laces 90, 100 (e.g., first lace 100 and second lace 90) and tensioning reels 91, 101, as appears in the rendered illustrations showing cable routing in the nonlimiting example of the right trans-radial embodiment of an internally cabled socket lacing system wherein the exposed flexible hinges are suitably emphasized. The flexible hinge includes a retention plate that provides a retaining force having at least a component vector urging the residual limb into the socket while providing the facility of allowing the elbow joint to rotate while maintaining compressive contact with the socket.

FIG. 14 is an illustration of medial and lateral counters, together with the elbow counter of a soft socket in the right trans-radial embodiment demonstrating lace routing to draw counters together in engagement to a limb at the elbow. The Right Transradial Embodiment of the OP Internally Cabled Elbow Counter and Supracondylar Cuff and Bone Interaction Medial View, shows the interaction of the stiff external counter and cuff and contoured internal supports with and the epicondyles of the humerus.

FIGS. 15A, and 15B are a series of rendered illustrations developing the soft socket lacing system layout showing A) the Balanced Hinge Lacing System 90', 90" (also referred to herein as second lace 90', 90") and B) the Top Lace System 100" (also referred to herein as first lace 100"), each in isolation. The Balanced Hinge Lacing System 90', 90" tightens the Medial and Lateral Counter rods together at the sides of the arm, and pulls the elbow counter 70 towards the forearm, drawing the residual limb into the socket. The two pairs of balanced hinges ensure that the socket is secure at every point during the full range of flexion and extension. The Top Lace System 100" also wraps behind the elbow counter 70, and then crosses over the anterior side of the limb, skirting the cubital fold, and crosses over several times to tighten the anterior side of the socket, pulling the Lateral and Medial Counters together.

FIG. 16 demonstrates the effects of elbow flexion as a flexion that varies tension based upon the respective position of first lace, or top lace, 100 and second lace, or hinge lace, 90 in showing the movement of the elbow at the neutral axis, and the balancing action of the flexible hinges in the right trans-radial embodiment of the internally cabled socket, with specific depiction of the axis of rotation and balancing flexible hinges. The anterior and posterior routings of the cable system extend and contract with the movement of the elbow, allowing freedom of movement. At the same time, the increase in the volume of the arm at flexion tightens the system and prevents gapping of the socket on the posterior side at full flexion.

FIGS. 17A and 17B are lateral and plan views, respectively, of the soft socket with all components showing the mutually supporting function of the four medial and lateral counter rods and the Top Lace 100 and Hinge Lace 90. Because the Top Lace 100 is routed on the anterior side of the limb, it tightens when the limb is extended, and is tightest at full extension, when the limb is most vulnerable and has the least inherent resistance to tensile loading. In contrast, the Balanced Hinge Lacing System 90' tightens when the limb is flexed, because of the volume change at the cubital fold, in combination with the excursion of the skin at the elbow. Despite the volume change, the shorter excursion on the anterior side of the elbow compensates for the greater excursion on the posterior side, and the tightening keeps the socket from gapping at the elbow.

Examples of disclosed prosthetic devices may be configured for use with lower limb residual limbs (e.g., in cases of transfemoral or transtibial amputations), while still including examples of elongate counters, variable compliance sockets, and lacing systems described herein. Such prosthetic devices may be configured to allow anatomical range of motion of lower limb joints by incorporating disclosed systems with components having different degrees of stiffness or compliance. Elongate counters may be configured to counter motion of itself relative to a portion of the residual limb in the same way that a shoe's heel counter prevents rearward motion of the heel during the heel strike. In examples of disclosed prosthetic devices configured for transfemoral or transtibial amputation, at least one elongate counter may be configured to resist motion relative to the residual limb on heel-strike while walking. Additionally or alternatively, at least one elongate counter may be configured to resist motion relative to the residual limb on toe-off while walking. In examples of disclosed prosthetic devices configured for transtibial amputations, the variable compliance socket may be configured to engage the knee joint. For example, the epicondyles of the femur may be engaged by the socket in such examples.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A prosthetic device for engaging a residual limb, the prosthetic device comprising:
a plurality of forearm counters extending proximally from a chassis and configured to receive at least a portion of the residual limb within a volume defined by the plurality of forearm counters, wherein each respective forearm counter of the plurality of forearm counters is configured to counteract forces applied to the residual limb via the prosthetic device, and wherein a wrist of the chassis at a distal end of the chassis is configured to operatively and removably couple a terminal device to the residual limb;
a variable compliance socket that is configured to conform to and engage with the residual limb, wherein the plurality of forearm counters are coupled to an outer surface of the variable compliance socket; and
a lacing system configured to secure the prosthetic device to the residual limb and configured to provide selective adjustment of compression of the variable compliance socket and the plurality of forearm counters around the residual limb, wherein the lacing system is coupled to the variable compliance socket such that the prosthetic device is configured to preserve a range of motion of the prosthetic device, wherein the lacing system comprises:
a first lace configured to automatically increase in tension in response to extension of the residual limb, wherein the first lace is further configured to automatically decrease in tension in response to flexion of the residual limb; and
a second lace configured to automatically increase in tension in response to flexion of the residual limb, wherein the second lace is further configured to automatically decrease in tension in response to extension of the residual limb.

2. The prosthetic device according to claim 1, wherein the first lace comprises a top lace that is routed on an anterior side of the variable compliance socket in a manner that is configured to avoid a cubital fold region of the residual limb, and wherein the second lace comprises a hinge lace that is routed along a medial side and a lateral side of the variable compliance socket.

3. The prosthetic device according to claim 2, further comprising an elbow counter configured to resist movement of an elbow of the residual limb away from the distal end of the chassis, and wherein the elbow counter comprises internal contoured padding.

4. The prosthetic device according to claim 3, wherein the top lace engages with the elbow counter and the plurality of forearm counters such that when the top lace is tightened, it pulls together a subset of the plurality of forearm counters positioned on an anterior side of the prosthetic device.

5. The prosthetic device according to claim 4, wherein the elbow counter comprises a first tensioning reel that is configured to selectively tighten or release the top lace, and wherein the top lace is continuous from the first tensioning reel to a distal end of the variable compliance socket.

6. The prosthetic device according to claim 3, wherein the internal contoured padding comprises:
  a first pad, wherein when the prosthetic device is worn, the first pad is configured to be positioned to support the medial epicondyle of the residual limb;
  a second pad, wherein when the prosthetic device is worn, the second pad is configured to be positioned to support the lateral epicondyle of the residual limb;
  and an olecranon fossa pad, wherein when the prosthetic device is worn, the olecranon fossa pad is configured to transfer forces between the elbow counter and the humerus of the residual limb.

7. The prosthetic device according to claim 3, wherein the hinge lace is configured to pull the elbow counter towards the plurality of forearm counters and draw the residual limb into the variable compliance socket.

8. The prosthetic device according to claim 7, wherein the chassis comprises a second tensioning reel adjacent the wrist, wherein the second tensioning reel is configured to selectively tighten or release the hinge lace, and wherein the hinge lace is continuous from the second tensioning reel to the elbow counter.

9. The prosthetic device according to claim 1, wherein the plurality of forearm counters are configured to maintain consistent attachment of the variable compliance socket on the residual limb, wherein the plurality of forearm counters are shaped and sized such that the plurality of forearm counters are configured to avoid impeding a range of movement of the residual limb while maintaining sufficient force to counter a load on the terminal device, and further wherein the plurality of forearm counters are configured to avoid applying pressure to pressure intolerant areas of the residual limb.

10. The prosthetic device according to claim 1, wherein the plurality of forearm counters form a generally double helix shape.

11. The prosthetic device according to claim 10, wherein the plurality of forearm counters comprises a lateral counter that is configured to be positioned with respect to the residual limb such that the lateral counter is configured to be positioned between the lateral epicondyle of the residual limb and the posterior proximal end of the ulna, wherein the lateral counter is configured to wrap distally and around the medial side of the forearm of the residual limb, wherein the lateral counter continues such that it is configured to cross the anterior side of the forearm over the radius and ulna to the lateral side of the radius and ulna at a distal tip of the residual limb, and further wherein the lateral counter continues distally to the wrist of the chassis.

12. The prosthetic device according to claim 11, wherein the plurality of forearm counters comprises a medial counter that is configured to be positioned with respect to the residual limb such that the medial counter is configured to be positioned between the lateral humeral epicondyle and the biceps tendon of the residual limb, wherein the medial counter is configured to continue distally along longitudinal axes of the radius and ulna of the residual limb, wherein the medial counter further continues by rotating laterally such that it is configured to be positioned behind the ulna and continue to the medial side of the forearm of the residual limb, and further wherein the medial counter continues distally to the wrist of the chassis.

13. The prosthetic device according to claim 1, further comprising interface padding positioned within the variable compliance socket and configured to be positioned between the plurality of forearm counters and the residual limb.

14. The prosthetic device according to claim 1, wherein the variable compliance socket comprises multiple layers that integrate with each other and with the plurality of forearm counters such that the variable compliance socket is configured to reinforce connection between the residual limb and the terminal device coupled to the chassis.

15. The prosthetic device according to claim 1, wherein the variable compliance socket is configured to be breathable and moisture-wicking.

16. The prosthetic device according to claim 1, wherein the lacing system comprises a plurality of cables or laces integrated into the variable compliance socket.

17. The prosthetic device according to claim 16, wherein the plurality of cables or laces of the lacing system pass through an elbow counter configured to resist movement of an elbow of the residual limb away from the distal end of the chassis.

18. A prosthetic device for engaging a residual limb, the prosthetic device comprising:
  a plurality of elongate counters extending proximally from a chassis and configured to receive at least a portion of the residual limb within a volume defined by the plurality of elongate counters, wherein each respective elongate counter of the plurality of elongate counters is configured to counteract forces applied to the residual limb via the prosthetic device, and wherein a distal end of the chassis is configured to operatively and removably couple a foot to the residual limb;
  a variable compliance socket that is configured to conform to and engage with the residual limb, wherein the plurality of elongate counters are coupled to an outer surface of the variable compliance socket; and
  a lacing system configured to secure the prosthetic device to the residual limb and configured to provide selective adjustment of compression of the variable compliance socket and the plurality of elongate counters around the residual limb, wherein the lacing system is coupled to the variable compliance socket such that the prosthetic device is configured to preserve a range of motion of the prosthetic device, wherein the lacing system comprises:
    a first lace configured to automatically increase in tension in response to extension of the residual limb, wherein the first lace is further configured to automatically decrease in tension in response to flexion of the residual limb; and
    a second lace configured to automatically increase in tension in response to flexion of the residual limb, wherein the second lace is further configured to automatically decrease in tension in response to extension of the residual limb.

19. The prosthetic device according to claim 18, wherein the prosthetic device is configured to engage the residual limb and the residual limb is the result of one or more selected from the group comprises a transfemoral amputation or a transtibial amputation.

20. The prosthetic device according to claim 18, wherein at least one elongate counter of the plurality of elongate counters is configured to resist motion relative to the residual limb on heel-strike while walking.

21. The prosthetic device according to claim 18, wherein at least one elongate counter of the plurality of elongate counters is configured to resist motion relative to the residual limb on toe-off while walking.

* * * * *